(12) United States Patent
Ruminiski et al.

(10) Patent No.: US 6,906,051 B2
(45) Date of Patent: Jun. 14, 2005

(54) LACTONE INTEGRIN ANTAGONISTS

(75) Inventors: Peter Ruminiski, Ballwin, MO (US); Thomas D. Penning, Elmhurst, IL (US); Lan Jiang, Ballwin, MO (US); Balekudru Devadas, Chesterfield, MO (US); Thomas Rogers, Ballwin, MO (US); Jennifer VanCamp, Glencoe, MO (US); Chester Yuan, Souther Oaks, CA (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 10/717,238

(22) Filed: Nov. 19, 2003

(65) Prior Publication Data

US 2004/0116472 A1 Jun. 17, 2004

Related U.S. Application Data

(62) Division of application No. 09/963,926, filed on Sep. 26, 2001, now Pat. No. 6,720,327.
(60) Provisional application No. 60/241,633, filed on Oct. 19, 2000, and provisional application No. 60/235,617, filed on Sep. 27, 2000.

(51) Int. Cl.[7] .................. A61K 31/33; A61K 31/505; C07D 239/00; C07D 407/00; C07D 305/00
(52) U.S. Cl. .................. 514/183; 514/514; 514/269; 514/256; 514/561; 514/482; 514/617; 514/473; 544/244; 544/297; 544/298; 544/322; 544/330; 544/335; 546/1; 549/263; 549/295; 549/321; 549/323
(58) Field of Search .................. 514/183, 269, 514/256, 561, 482, 617, 449, 473; 544/224, 297, 298, 322, 330, 335; 546/1; 549/263, 295, 321, 323

(56) References Cited

U.S. PATENT DOCUMENTS

| | | | |
|---|---|---|---|
| 5,602,155 A | | 2/1997 | Ruminski .................. 514/357 |
| 6,013,651 A | | 1/2000 | Rogers et al. .............. 514/269 |
| 6,028,223 A | * | 2/2000 | Ruminski et al. ............. 564/27 |
| 6,211,191 B1 | | 4/2001 | Duggan et al. ............. 514/274 |
| 6,720,327 B2 | * | 4/2004 | Ruminski et al. ........... 514/269 |

FOREIGN PATENT DOCUMENTS

| | | | | |
|---|---|---|---|---|
| EP | 0641800 | | 1/1994 | ............ C07K/5/06 |
| WO | 9708145 | * | 3/1997 | |

OTHER PUBLICATIONS

U.S. Appl. No. 10/381,834, filed Aug. 23, 2003.*
Cecil Textbook of Medicine, 20th Edition, vol. 1,1004–10(1996).*
Uckun et al, Current cancer Drug Targets,1/1,59–71(2001).*
PubMed 12082286,also cited as Biorheology,39/1–2, 237–46(2002).*
PubMed Abstract 12851778,also cited as Acta Neuropathol. (Berl) 106/4,319–22(2003).*
PubMed Abstract 12234368,also cited as Immunol. Rev. 186, 125–40(2002).*
PubMed Abstract 14718670, also cited as Proc. Natl. Acad. Sci.USA, 101/3,763–8(2004).*
PubMed Abstract 10723092, also cited as Cell Biochem. 77/2,265–76(2000).*
PubMed Abstract 12657612, also cited as Invest. Ophthalmol. Vis. Sci. 44/4,1704–15(2003).*
Carron, et al., *Cancer Research*; V. 58, No. 9: pp. 1930–1935; 1998.
Lark, et al., *Journal of Bone & Mineral Research*; V. 16, No. 2: pp. 319–327; 2000.
Healy, et al., *Human Reproductive Update*; V. 4: pp. 136; 1998.
Cheresh, *Cancer Metastasis Review*; V. 10: pp. 3–10; 1991.
Brooks, et al., *Cell*; V. 79, No. 7: pp. 1157–1164; 1994.
Friedlander, et al., *Proceedings Of The National Academy Of Science USA*; V. 93, No. 18; pp. 9764–9769; 1996.
Badger, et al., *Arthritis & Rheumatism*; V. 44, No. 1: pp. 128–137; 2001.
Brown, *Cardiovascular Research*; V. 28; pp. 1815–; 1994.
Friedlander, et al., *Science*; V. 270 (5241): pp. 1500–1502; 1995.
Agrez, et al., *Journal of Cell Biology*; V. 127, No. 2: pp. 547–556; 1994.
Christofidou–Solomidou, et al., *American Journal of Pathology*; V. 151 (4): pp. 975–983; 1997.
Seftor, et al., *Proceedings of the National Academy of Science USA*; V. 89: pp. 1557–1561;Mar. 1992.
Montgomery, et al., *Proceedings of the National Academy of Science USA*; V. 91: pp. 8856–8860; Sep. 1994.
Adamis, et al., *American Journal of Ophthalmology*; V. 118: pp. 445–450; 1994.

(Continued)

Primary Examiner—Richard L. Raymond
Assistant Examiner—Sudhaker B. Patel
(74) Attorney, Agent, or Firm—Harness, Dickey & Pierce, LLP

(57) ABSTRACT

The present invention relates to a class of compounds represented by the Formula I:

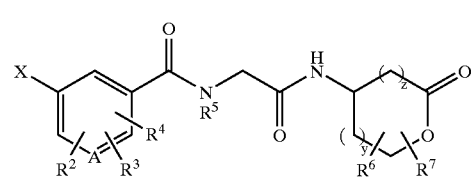

or a pharmaceutically acceptable salt thereof, pharmaceutical compositions comprising compounds of the Formula I, and methods of selectively inhibiting or antagonizing the $\alpha_v\beta_3$ and/or the $\alpha_v\beta_5$ integrin.

12 Claims, No Drawings

OTHER PUBLICATIONS

Peacock, et al., *Journal of Experimental Medicine*; V. 175: pp. 1135–1138; 1992.
Brooks, et al., *Science*; V. 264: pp 569–571; 1994.
Sato, et al., *Journal of Cell Biology*; V. 111: pp. 1713–1723; 1990.
Fisher, et al., *Endocrinology*; V. 132: pp. 1411–1413; 1993.
Choi, et al., *Journal of Vascular Surgery*; V. 19(1): pp. 125–134; 1994.
White, *Current Biology*; V. 3(9): pp 596–599; 1993.
Rodriquez, et al., *Tetrahedron Letters*; V. 32(7): pp. 923–926; 1991.
*Design in Prodrugs*, H. Bundgaard, editor; Elsevier; 1985.
Pytela, et al., *Methods in Enzymology*, V. 144: pp. 475–489; 1987.
Yatohgo, et al., *Cell Structure & Function*; V. 13: pp. 281–292; 1988.
Charo, et al., *Journal of Biological Chemistry*; V. 266(3): pp. 1415–1421; 1991.
Niya, et al., *Blood*, V. 70(2): pp. 475–483; 1987.
Rodbard, et al., *International Atomic Energy Agency, Vienna*; pp 469–; 1977.
Zucker, *Methods in Enzymology*; V. 169; pp. 117–133; 1989.

* cited by examiner

LACTONE INTEGRIN ANTAGONISTS

This application is a divisional application of U.S. Pat. No. 6,720,327 (issued Apr. 13, 2004; filed as U.S. application Ser. No. 09/963,926 on Sep. 26, 2001), which claimed priority under Title 35, United States Code §119 of U.S. Provisional Applications Ser. No. 60/235,617, filed Sep. 27, 2000, and Ser. No. 60/241,633, filed Oct. 19, 2000, both now abandoned.

FIELD OF THE INVENTION

The present invention relates to pharmaceutical agents which are $\alpha_v\beta_3$ and/or $\alpha_v\beta_5$ integrin antagonists and as such are useful in pharmaceutical compositions and in methods for treating conditions mediated by $\alpha_v\beta_3$ and/or $\alpha_v\beta_5$ integrins.

BACKGROUND OF THE INVENTION

Integrins are a group of cell surface glycoproteins which mediate cell adhesion and therefore are useful mediators of cell adhesion interactions which occur during various biological processes. Integrins are heterodimers composed of noncovalently linked α and β polypeptide subunits. Currently eleven different α subunits have been identified and six different β subunits have been identified. The various α subunits can combine with various β subunits to form distinct integrins.

The integrin identified as $\alpha_v\beta_3$ (also known as the vitronectin receptor) has been identified as an integrin which plays a role in various conditions or disease states including tumor metastasis, solid tumor growth (neoplasia), osteoporosis (Ross, et al., *J. Biol, Chem.*, 1987, 262, 7703), Paget's disease, humoral hypercalcemia of malignancy (Carron et al., *Cancer Res.* 1998, 58, 1930), osteopenia (Lark et al., *J Bone Miner Res.* 2001,16, 319), endometriosis (Healy et al., *Hum. Reproductive Update*, 1998, 4, 736), angiogenesis, including tumor angiogenesis (Cheresh, *Cancer Metastasis Rev.*, 1991, 10, 3–10 and Brooks, et al., *Cell*, 1994, 79, 1157), retinopathy including macular degeneration (Friedlander et al., *Proc. Natl. Acad. Sci USA* 1996, 93, 9764), arthritis, including rheumatoid arthritis (Badger et al., *Arthritis Rheum*, 2001, 44, 128), periodontal disease, psoriasis and smooth muscle cell migration (e.g. restenosis and artherosclerosis, (Brown et al., *Cardiovascular Res.*, 1994, 28, 1815). The compounds of the present invention are $\alpha_v\beta_3$ antagonists and can be used, alone or in combination with other therapeutic agents, in the treatment or modulation of various conditions or disease states described above. Additionally, it has been found that such agents would be useful as antivirals, antifungals and antimicrobials. Thus, compounds which selectively antagonize $\alpha_v\beta_3$ would be beneficial for treating such conditions.

The integrin $\alpha_v\beta_5$ plays a role in neovascularization. Antagonists of the $\alpha_v\beta_5$ integrin will inhibit neovascularization and will be useful for treating and preventing angiogenesis metastasis, tumor growth, macular degeneration and diabetic retionopathy. M. C. Friedlander, et al., *Science*, 270, 1500–1502 (1995) disclose that a monoclonal antibody for $\alpha_v\beta_5$ inhibits VEFG-induced angogenesis in the rabbit cornea and the chick chorioallantoic membrane model. Therefore, it would be useful to antagonize both the $\alpha_v\beta_5$ and the $\alpha_v\beta_3$ receptor. Such "mixed $\alpha_v\beta_5/\alpha_v\beta_3$ antagonists" or "dual $\alpha_v\beta_3/\alpha_v\beta_5$ antagonists" would be useful for treating or preventing angiogenesis, tumor metastasis, tumor growth, diabetic retinopathy, macular degeneration, atherosclerosis and osteoporosis.

It has been shown that the $\alpha_v\beta_3$ integrin and other $\alpha_v$ containing integrins bind to a number of Arg-Gly-Asp (RGD) containing matrix macromolecules. Compounds containing the RGD sequence mimic extracellular matrix ligands so as to bind to cell surface receptors. However, it is also known that RGD peptides in general are non-selective for RGD dependent integrins. For example, most RGD peptides which bind to $\alpha_v\beta_3$ also bind to $\alpha_v\beta_5$, $\alpha_v\beta_1$ and $\alpha_{IIb}\beta_3$. Antagonism of platelet $\alpha_{IIb}\beta_3$ (also known as the fibrinogen receptor) is known to block platelet aggregation in humans. In order to avoid bleeding side-effects when treating the conditions or disease states associated with the integrin $\alpha_v\beta_3$, it would be beneficial to develop compounds which are selective antagonists of $\alpha_v\beta_3$ as opposed to $\alpha_{IIb}\beta_3$.

Further, it has not been established in the art that sparing $\alpha_v\beta_6$ integrin would be a beneficial property to be incorporated in the design of antagonists of $\alpha_v\beta_3$. Rather, $\alpha_v\beta_6$ has been identified as a target for antagonists because it is higly expressed in many carcinoma cell lines, and has been shown to enchance the proliferative capacity of a colon carcinoma cell line both in vivo and in vitro (Agrez et al., 1994, *J. Cell Biol.* 127, 547). Additionally, $\alpha_v\beta_6$ is expressed during the later stages of wound healing and remains expressed until the wound is closed (See Christofidou-Solomidou, et al., 1997 *American J. of Pathol.*, 151, 975), and therefore it is believed that $\alpha_v\beta_6$ plays a role in the remodeling of the vasculature during the later stages of angiogenesis. Accordingly, antagonists of $\alpha_v\beta_6$ are seen as useful in treating or preventing cancer by inhibiting tumor growth and metastasis (see, for example, U.S. Pat. No. 6,211,191).

Tumor cell invasion occurs by a three step process: 1) tumor cell attachment to extracellular matrix; 2) proteolytic dissolution of the matrix; and 3) movement of the cells through the dissolved barrier. This process can occur repeatedly and can result in metastases at sites distant from the original tumor.

Seftor et al. (*Proc. Natl. Acad Sci. USA*, Vol. 89 (1992) 1557–1561) have shown that the $\alpha_v\beta_3$ integrin has a biological function in melanoma cell invasion. Montgomery et al., (*Proc. Natl. Acad. Sci. USA*, Vol. 91 (1994) 8856–60) have demonstrated that the integrin $\alpha_v\beta_3$ expressed on human melanoma cells promotes a survival signal, protecting the cells from apoptosis. Mediation of the tumor cell metastatic pathway by interference with the $\alpha_v\beta_3$ integrin cell adhesion receptor to impede tumor metastasis would be beneficial.

Brooks et al. (*Cell*, Vol. 79 (1994) 1157–1164) have demonstrated that antagonists of $\alpha_v\beta_3$ provide a therapeutic approach for the treatment of neoplasia (inhibition of solid tumor growth) since systemic administration of $\alpha_v\beta_3$ antagonists causes dramatic regression of various histologically distinct human tumors.

The adhesion receptor integrin $\alpha_v\beta_3$ was identified as a marker of angiogenic blood vessels in chick and man and therefore such receptor plays a critical role in angiogenesis or neovascularization. Angiogenesis is characterized by the invasion, migration and proliferation of smooth muscle and endothelial cells. Antagonists of $\alpha_v\beta_3$ inhibit this process by selectively promoting apoptosis of cells in neovasculature. The growth of new blood vessels, or angiogenesis, also contributes to pathological conditions such as diabetic retinopathy including macular degeneration (Adamis et al., *Amer. J. Ophthal.*, Vol. 118, (1994) 445–450) and rheumatoid arthritis (Peacock et al., *J. Exp. Med.*, Vol. 175, (1992), 1135–1138). Therefore, $\alpha_v\beta_3$ antagonists would be useful therapeutic agents for treating such conditions associated with neovasculanization (Brooks et al., *Science*, Vol. 264, (1994), 569–571).

It has been reported that the cell surface receptor $\alpha_V\beta_3$ is the major integrin on osteoclasts responsible for attachment to bone. Osteoclasts cause bone resorption and when such bone resorbing activity exceeds bone forming activity it results in osteoporosis (loss of bone), which leads to an increased number of bone fractures, incapacitation and increased mortality. Antagonists of $\alpha_V\beta_3$ have been shown to be potent inhibitors of osteoclastic activity both in vitro [Sato et al., *J. Cell. Biol.*, Vol. 111 (1990) 1713–1723] and in vivo [Fisher et al., *Endocrinology*, Vol. 132 (1993) 1411–1413]. Antagonism of $\alpha_V\beta_3$ leads to decreased bone resorption and therefore restores a normal balance of bone forming and resorbing activity. Thus it would be beneficial to provide antagonists of osteoclast $\alpha_V\beta_3$ which are effective inhibitors of bone resorption and therefore are useful in the treatment or prevention of osteoporosis.

The role of the $\alpha_V\beta_3$ integrin in smooth muscle cell migration also makes it a therapeutic target for prevention or inhibition of neointimal hyperplasia which is a leading cause of restenosis after vascular procedures (Choi et al., *J. Vasc. Surg.* Vol. 19(1) (1994) 125–34). Prevention or inhibition of neointimal hypeplasia by pharmaceutical agents to prevent or inhibit restenosis would be beneficial.

White (*Current Biology*, Vol. 3(9)(1993) 596–599) has reported that adenovirus uses $\alpha_V\beta_3$ for entering host cells. The integrin appears to be required for endocytosis of the virus particle and may be required for penetration of the viral genome into the host cell cytoplasm. Thus compounds which inhibit $\alpha_V\beta_3$ would find usefulness as antiviral agents.

SUMMARY OF THE INVENTION

The compounds of this invention are 1) $\alpha_V\beta_3$ integrin antagonists; or 2) $\alpha_V\beta_5$ integrin antagonists; or 3) mixed or dual $\alpha_V\beta_3/\alpha_V\beta_5$ antagonists. The present invention includes compounds which inhibit the respective integrins and also includes pharmaceutical compositions comprising such compounds. The present invention further provides for methods for treating or preventing conditions mediated by the $\alpha_V\beta_3$ and/or $\alpha_V\beta_5$ receptors in a mammal in need of such treatment comprising administering a therapeutically effective amount of the compounds of the present invention and pharmaceutical compositions of the present invention. Administration of such compounds and compositions of the present invention inhibits angiogenesis, tumor metastasis, tumor growth, osteoporosis, Paget's disease, humoral hypercalcemia of malignancy, retinopathy, macular degeneration, arthritis, periodontal disease, smooth muscle cell migration, including restenosis and artherosclerosis, and viral diseases.

The compounds of the present invention further show greater selectivity for the $\alpha_V\beta_3$ and/or $\alpha_V\beta_5$ integrin than for the $\alpha_V\beta_6$ integrin. It has been found that the selective antagonism of the $\alpha_V\beta_3$ integrin is desirable in that the $\alpha_V\beta_6$ integrin may play a role in normal physiological processes of tissue repair and cellular turnover that routinely occur in the skin and pulmonary tissue, and the inhibition of this function can be deleterious. Therefore, compounds of the present invention which selectively inihibit the $\alpha_V\beta_3$ integrin as opposed to the $\alpha_V\beta_6$ integrin have reduced side-effects associated with inhibtion of the $\alpha_V\beta_6$ integrin.

The present invention relates to a class of compounds represented by the Formula I.

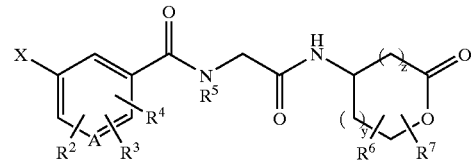

I or a pharmaceutically acceptable salts thereof wherein
X is

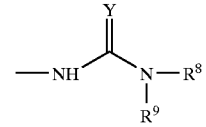

Y is selected from the group consisting of N—$R^1$, O, and S;
y and z are independently selected from an integer selected form 0, 1, 2 and 3;
A is N or C;
$R^1$ is selected from the group consisting of H, alkyl, aryl, hydroxy, alkoxy, cyano, nitro, amino, alkenyl, alkynyl, amido, alkylcarbonyl, arylcarbonyl, alkoxycarbonyl, aryloxycarbonyl, haloalkylcarbonyl, haloalkoxycarbonyl, alkylthiocarbonyl, arylthiocarbonyl, acyloxymethoxycarbonyl, alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles, aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle, monocyclic heterocycles, and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or
$R^1$ taken together with $R^8$ forms a 4–12 membered dinitrogen containing heterocycle optionally substituted with one or more substituent selected from the group consisting of lower alkyl, hydroxy, keto, alkoxy, halo, phenyl, amino, carboxyl or carboxyl ester, and fused phenyl; or
$R^1$ taken together with $R^8$ forms a 5 membered heteroaromatic ring optionally substituted with one or more substituent selected from lower alkyl, phenyl and hydroxy; or
$R^1$ taken together with $R^8$ forms a 5 membered heteroaromatic ring fused with a phenyl group;
$R^8$ (when not taken together with $R^1$) and $R^9$ are independently selected from the group consisting of H, alkyl, alkenyl, alkynyl, aralkyl, amino, alkylamino, hydroxy, alkoxy, arylamino, amido, alkylcarbonyl, arylcarbonyl, alkoxycarbonyl, aryloxy, aryloxycarbonyl, haloalkylcarbonyl, haloalkoxycarbonyl, alkylthiocarbonyl, arylthiocarbonyl, acyloxymethoxycarbonyl, cycloalkyl, bicycloalkyl, aryl, acyl, benzoyl, alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles, monocyclic heterocycles, monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl, monocyclic and bicyclic heterocyclicalkyls, —SO₂R¹⁰ wherein R¹⁰ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylaamino, alkylamino, dialkylamino, trifluoromethylthio, trifluoroalkoxy, trifluoromethylsulfonyl, aryl, aryloxy, thio, alkylthio, and monocyclic heterocycles; and

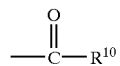

wherein R¹⁰ is defined as above; or
NR⁸ and R⁹ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;
or
X is

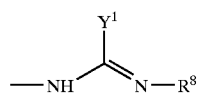

wherein Y' is selected from the group consisting of alkyl, cycloalkyl, bicycloalkyl, aryl, monocyclic heterocycles, alkyl optionally substituted with aryl which can also be optionally substituted with one or more substituent selected from halo, haloalkyl, alkyl, nitro, hydroxy, alkoxy, aryloxy, aryl, or fused aryl, aryl optionally substituted with one or more substituent selected from halo, haloalkyl, hydroxy, alkoxy, aryloxy, aryl, fused aryl, nitro, methylenedioxy, ethylenedioxy, or alkyl, alkynyl, alkenyl, —S—R¹¹ and —OR¹¹ wherein R¹¹ is selected from the group consisting of H, alkyl, aralkyl, aryl, alkenyl, and alkynyl, or R¹¹ taken together with R⁸ forms a 4–12 membered mononitrogen and monosulfur or monooxygen containing heterocyclic ring optionally substituted with lower alky, hydroxy, keto, phenyl, carboxyl or carboxyl ester, and fused phenyl, or R¹¹ taken together with R⁸ is thiazole, oxazole, betizoxazole, or benzothiazole;
R⁸ is defined as above; or
Y¹ (when Y¹ is carbon) taken together with R⁸ forms a 4–12 membered mononitrogen or dinitrogen containing ring optionally substituted with alkyl, aryl, keto or hydroxy; or
X is

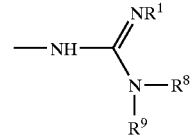

wherein R¹ and R⁸ taken together form a 5–8 membered dinitrogen containing heterocycle optionally substituted with one or more substituent selected from the group consisting of lower alkyl, hydroxy, keto, phenyl, or carboxyl derivatives; and R⁹ is selected from the group consisting of alkylcarbonyl, arylcarbonyl, alkoxycarbonyl, aryloxycarbonyl, haloalkylcarbonyl, haloalkoxycarbonyl, alkylthiocarbonyl, arylthiocarbonyl, or acyloxymethoxycarbonyl; or
X is

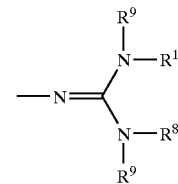

wherein R¹ and R⁸ taken together form a 5–8 membered dinitrogen containing heterocycle optionally substituted with hydroxy, keto, phenyl, or alkyl; and R⁹ are both selected from the group consisting of alkylcarbonyl, arylcarbonyl, alkoxycarbonyl, aryloxycarbonyl, haloalkylcarbonyl, haloalkoxycarbonyl, alkylthiocarbonyl, arylthiocarbonyl and acyloxymethoxycarbonyl;
R², R³ and R⁴ are independently selected from one or more substituent selected from thegroup consisting of H, alkyl, hydroxy, alkoxy, aryloxy, halogen, haloalkyl, haloalkoxy, nitro, amino, alkylamino, acylamino, dialkylamino, cyano, alkylthio, alkylsulfonyl, carboxyl derivatives, trihaloacetamide, acetamide, aryl, fused aryl, cycloalkyl, thio, monocyclic heterocycles, fused monocyclic heterocycles, and X, wherein X is defined as above;
R⁵, R⁶ and R⁷ are independently selected from the group consisting of hydrogen, alkyl, alkenyl, alkynyl, aryl, carboxyl derivatives, haloalkyl, cycloalkyl, monocyclic heterocycles, monocyclic heterocycles optionally substituted with alkyl, halogen, haloalkyl, cyano, hydroxy, aryl, fused aryl, nitro, alkoxy, aryloxy, alkylsulfonyl, arylsulfonyl, sulfonamide, thio, alkylthio, carboxyl derivatives, amino, amido, alkyl optionally substituted with one or more of halo, haloalkyl, hydroxy, alkoxy, aryloxy, thio, alkylthio, alkynyl, alkenyl, alkyl, arylthio, alkylsulfoxide, alkylsulfonyl, arylsulfoxide, arylsulfonyl, cyano, nitro, amino, alkylamino, dialkylamino, alkylsulfonamide, arylsulfonamide, acylamide, carboxyl derivatives, sulfonamide, sulfonic acid, phosphonic acid derivatives, phosphinic acid derivatives, aryl, arylthio, arylsulfoxide, or arylsulfone all optionally substituted on the aryl ring with halo, alkyl, haloalkyl, cyano, nitro, hydroxy, carboxyl derivatives, alkoxy, aryloxy, amino, alkylamino, dialkylamino, amido, aryl, fused aryl, monocyclic heterocycles, and fused monocyclic heterocycles, monocyclic heterocyclicthio, monocyclic heterocyclicsulfoxide, and monocyclic heterocyclic sulfone, which can be optionally substituted with halo, haloalkyl, nitro, hydroxy, alkoxy, fused aryl, or alkyl, alkylcarbonyl, haloalkylcarbonyl, and arylcarbonyl, aryl optionally substituted in one or more positions with halo, haloalkyl, alkyl, alkoxy, aryloxy, methylenedioxy, ethylenedioxy, alkylthio, haloalkylthio, thio, hydroxy, cyano, nitro, acyloxy, carboxyl derivatives, carboxyalkoxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles and fused monocyclic heterocycles.

The compounds according to Formula I can exist in various isomers, enantiomers, tautomers, racemates and polymorphs, and all such forms are meant to be included.

It is another object of the invention to provide pharmaceutical compositions comprising compounds of the Formula I. Such compounds and compositions are useful in selectively inhibiting or antagonizing the $\alpha_v\beta_3$ and/or $\alpha_v\beta_5$ integrins and therefore in another embodiment the present invention relates to a method of selectively inhibiting or antagonizing the $\alpha_v\beta_3$ and/or $\alpha_v\beta_5$ integrin. The invention further involves treating or inhibiting pathological conditions associated therewith such as osteoporosis, humoral hypercalcemia of malignancy, Paget's disease, tumor metastasis, solid tumor growth (neoplasia), angiogenesis, including tumor angiogenesis, retinopathy including macular degeneration and diabetic retinopathy, arthritis, including rheumatoid arthritis, periodontal disease, psoriasis, smooth muscle cell migration and restenosis in a mammal in need of such treatment. Additionally, such pharmaceutical agents are useful as antiviral agents, and antimicrobials.

DETAILED DESCRIPTION

In its broadest sense, the invention relates to compounds represented by Formula I The present invention relates to compound represented by Formula I

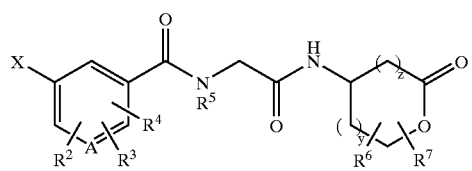

I or a pharmaceutically acceptable salts thereof wherein
X is

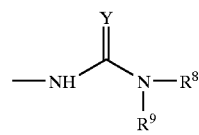

Y is selected from the group consisting of N—$R^1$, O, and S;
y and z are independently selected from an integer selected form 0, 1, 2 and 3;
A is N or C;
$R^1$ is selected from the group consisting of H, alkyl, aryl, hydroxy, alkoxy, cyano, nitro, amino, alkenyl, alkynyl, amido, alkylcarbonyl, arylcarbonyl, alkoxycarbonyl, aryloxycarbonyl, haloalkylcarbonyl, haloalkoxycarbonyl, alkylthiocarbonyl, arylthiocarbonyl, acyloxymethoxycarbonyl, alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles, aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle, monocyclic heterocycles, and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or $R^1$ taken together with $R^8$ forms a 4–12 membered dinitrogen containing heterocycle optionally substituted with one or more substituent selected from the group consisting of lower alkyl, hydroxy, keto, alkoxy, halo, phenyl, amino, carboxyl or carboxyl ester, and fused phenyl; or $R^1$ taken together with $R^8$ forms a 5 membered heteroaromatic ring optionally substituted with one or more substituent selected from lower alkyl, phenyl and hydroxy; or $R^1$ taken together with $R^8$ forms a 5 membered heteroaromatic ring fused with a phenyl group;

$R^8$ (when not taken together with $R^1$) and $R^9$ are independently selected from the group consisting of H, alkyl, alkenyl, alkynyl, aralkyl, amino, alkylamino, hydroxy, alkoxy, arylamino, amido, alkylcarbonyl, arylcarbonyl, alkoxycarbonyl, aryloxy, aryloxycarbonyl, haloalkylcarbonyl, haloalkoxycarbonyl, alkylthiocarbonyl, arylthiocarbonyl, acyloxymethoxycarbonyl, cycloalkyl, bicycloalkyl, aryl, acyl, benzoyl, alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles, aryl optionally substituted withone or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles, monocyclic heterocycles, monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl, monocyclic and bicyclic heterocyclicalkyls, —SO$_2$R$^{10}$ wherein R$^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

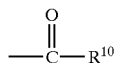

wherein R$^{10}$ is defined as above; or
NR$^8$ and R$^9$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;
or
X is

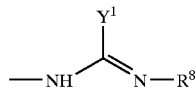

wherein Y' is selected from the group consisting of alkyl, cycloalkyl, bicycloalkyl, aryl, monocyclic heterocycles, alkyl optionally substituted with aryl which can also be optionally substituted with one or more substituent selected from halo, haloalkyl, alkyl, nitro, hydroxy, alkoxy, aryloxy, aryl, or fused aryl, aryl optionally substituted with one or more substituent selected from halo, haloalkyl, hydroxy, alkoxy, aryloxy, aryl, fused aryl, nitro, methylenedioxy, ethylenedioxy, or alkyl, alkynyl, alkenyl, —S—R$^{11}$ and —OR$^{11}$ wherein R$^{11}$ is selected from the group consisting of H, alkyl, aralkyl, aryl, alkenyl, and alkynyl, or R$^{11}$ taken together with R$^8$ forms a 4–12 membered mononitrogen and monosulfur or monooxygen containing heterocyclic ring optionally substituted with lower alkyl, hydroxy, keto, phenyl, carboxyl or carboxyl ester, and fused phenyl, or R$^{11}$ taken together with R$^8$ is thiazole, oxazole, benzoxazole, or benzothiazole;
R$^8$ is defined as above; or
Y$^1$ (when Y$^1$ is carbon) taken together with R$^8$ forms a 4–12 membered mononitrogen or dinitrogen containing ring optionally substituted with alkyl, aryl, keto or hydroxy; or
X is

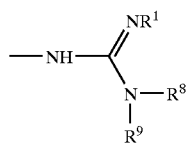

wherein R$^1$ and R$^8$ taken together form a 5–8 membered dinitrogen containing heterocycle optionally substituted with one or more substituent selected from the group consisting of lower alkyl, hydroxy, keto, phenyl, or carboxyl derivatives; and R$^9$ is selected from the group consisting of alkylcarbonyl, arylcarbonyl, alkoxycarbonyl, aryloxycarbonyl, haloalkylcarbonyl, haloalkoxycarbonyl, alkylthiocarbonyl, arylthiocarbonyl, or acyloxymethoxycarbonyl; or X is

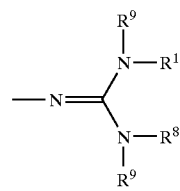

wherein R$^1$ and R$^8$ taken together form a 5–8 membered dinitrogen containing heterocycle optionally substituted with hydroxy, keto, phenyl, or alkyl; and R$^9$ are both selected from the group consisting of alkylcarbonyl, arylcarbonyl, alkoxycarbonyl, aryloxycarbonyl, haloalkylcarbonyl, haloalkoxycarbonyl, alkylthiocarbonyl, arylthiocarbonyl and acyloxymethoxycarbonyl;

R$^2$, R$^3$ and R$^4$ are independently selected from one or more substituent selected from thegroup consisting of H, alkyl, hydroxy, alkoxy, aryloxy, halogen, haloalkyl, haloalkoxy, nitro, amino, alkylamino, acylamino, dialkylamino, cyano, alkylthio, alkylsulfonyl, carboxyl derivatives, trihaloacetamide, acetamide, aryl, fused aryl, cycloalkyl, thio, monocyclic heterocycles, fused monocyclic heterocycles, and X, wherein X is defined as above;

R$^5$, R$^6$ and R$^7$ are independently selected from the group consisting of hydrogen, alkyl, alkenyl, alkynyl, aryl, carboxyl derivatives, haloalkyl, cycloalkyl, monocyclic heterocycles, monocyclic heterocycles optionally substituted with alkyl, halogen, haloalkyl, cyano, hydroxy, aryl, fused aryl, nitro, alkoxy, aryloxy, alkylsulfonyl, arylsulfonyl, sulfonamide, thio, alkylthio, carboxyl derivatives, amino, amido, alkyl optionally substituted with one or more of halo, haloalkyl, hydroxy, alkoxy, aryloxy, thio, alkylthio, alkynyl, alkenyl, alkyl, arylthio, alkylsulfoxide, alkylsulfonyl, arylsulfoxide, arylsulfonyl, cyano, nitro, amino, alkylamino, dialkylamino, alkylsulfonamide, arylsulfonamide, acylamide, carboxyl derivatives, sulfonamide, sulfonic acid, phosphonic acid derivatives, phosphinic acid derivatives, aryl, arylthio, arylsulfoxide, or arylsulfone all optionally substituted on the aryl ring with halo, alkyl, haloalkyl, cyano, nitro, hydroxy, carboxyl derivatives, alkoxy, aryloxy, amino, alkylamino, dialkylamino, amido, aryl, fused aryl, monocyclic heterocycles, and fused monocyclic heterocycles, monocyclic heterocyclicthio, monocyclic heterocyclicsulfoxide, and monocyclic heterocyclic sulfone, which can be optionally substituted with halo, haloalkyl, nitro, hydroxy, alkoxy, fused aryl, or alkyl, alkylcarbonyl, haloalkylcarbonyl, and arylcarbonyl, aryl optionally substituted in one or more positions with halo, haloalkyl, alkyl, alkoxy, aryloxy, methylenedioxy, ethylenedioxy, alkylthio, haloalkylthio, thio, hydroxy, cyano, nitro, acyloxy, carboxyl derivatives, carboxyalkoxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles and fused monocyclic heterocycles.

In another embodiment, the invention is represented by Formula II

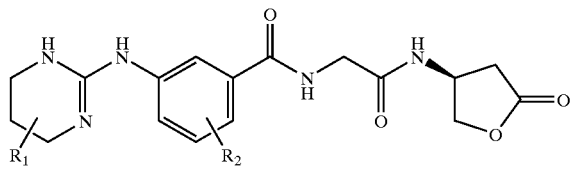

or a pharmaceutically acceptable salt thereof, wherein $R_1$ and $R_2$ are selected from a group consisting of hydrogen, hydroxy alkyl haloalkyl and halogen.

The invention further relates to pharmaceutical compositions containing therapeutically effective amounts of the compounds of Formula I or II.

The invention also relates to a method of selectively inhibiting or antagonizing the $\alpha_v\beta_3$ integrin and/or the $\alpha_v\beta_5$ integrin and more specifically relates to a method of inhibiting bone resorption, periodontal disease, osteoporosis, humoral hypercalcemia of malignancy, Paget's disease, tumor metastasis, solid tumor growth (neoplasia), angiogenesis, including tumor angiogenesis, retinopathy including macular degeneration and diabetic retinopathy, arthritis, including rheumatoid arthritis, smooth muscle cell migration and restenosis by administering a therapeutically effective amount of a compound of the Formula I to achieve such inhibition together with a pharmaceutically acceptable carrier. More specifically it has been found that it advantageous to administer compounds which are $\alpha_v\beta_3$ and/or $\alpha_v\beta_5$ antagonists which compounds selectively inhibit the $\alpha_v\beta_3$ and/or $\alpha_v\beta_5$ integrin as opposed to the $\alpha_v\beta_6$ integrin. It has now been found that such selectivity is beneficial in reducing unwanted side-effects.

To evaluate the selectivity of compounds between the integrins $\alpha_v\beta_3$ and $\alpha_v\beta_6$, cell-based assays are established using the 293 human embryonic kidney cell line as described herein. The compounds disclosed herein have shown significant selectivity between the integrins $\alpha_v\beta_3$ and $\alpha_v\beta_6$. The selective antagonism of the $\alpha_v\beta_3$ integrin is viewed as desirable in this class of compounds, as $\alpha_v\beta_6$ may also play a role in normal physiological processes of tissue repair and cellular turnover that routinely occur in the skin and pulmonary tissues.

As used herein, the terms "alkyl" or "lower alkyl" refer to a straight chain or branched chain hydrocarbon radicals having from about 1 to about 10 carbon atoms, and more preferably 1 to about 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein the terms "alkenyl" or "lower alkenyl" refer to unsaturated acyclic hydrocarbon radicals containing at least one double bond and 2 to about 6 carbon atoms, which carbon-carbon double bond may have either cis or trans geometry within the alkenyl moiety, relative to groups substituted on the double bond carbons. Examples of such groups are ethenyl, propenyl, butenyl, isobutenyl, pentenyl, hexenyl and the like.

As used herein the terms "alkynyl" or "lower alkynyl" refer to acyclic hydrocarbon radicals containing one or more triple bonds and 2 to about 6 carbon atoms. Examples of such groups are ethynyl, propynyl, butynyl, pentynyl, hexynyl and the like.

The term "cycloalkyl" as used herein means saturated or partially unsaturated cyclic carbon radicals containing 3 to about 8 carbon atoms and more preferably 4 to about 6 carbon atoms. Examples of such cycloalkyl radicals include cyclopropyl, cyclopropenyl, cyclobutyl, cyclopentyl, cyclohexyl, 2-cyclohexen-1-yl, and the like.

The term "aryl" as used herein denotes aromatic ring systems composed of one or more aromatic rings. Preferred aryl groups are those consisting of one, two or three aromatic rings. The term embraces aromatic radicals such as phenyl, pyridyl, naphthyl, thiophene, furan, biphenyl and the like.

As used herein, the term "cyano" is represented by a radical

The terms "hydroxy" and "hydroxyl" as used herein are synonymous and are represented by a radical

The term "lower alkylene" or "alkylene" as used herein refers to divalent linear or branched saturated hydrocarbon radicals of 1 to about 6 carbon atoms.

As used herein the term "alkoxy" refers to straight or branched chain oxy containing radicals. Examples of alkoxy groups encompassed include methoxy, ethoxy, n-propoxy, n-butoxy, isopropoxy, isobutoxy, sec-butoxy, t-butoxy and the like.

As used herein the terms "arylalkyl" or "aralkyl" refer to a radical of the formula

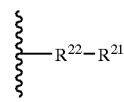

1 wherein $R^{21}$ is aryl as defined above and $R^{22}$ is an alkylene as defined above. Examples of aralkyl groups include benzyl, pyridylmethyl, naphthylpropyl, phenethyl and the like.

As used herein the term "nitro" is represented by a radical

As used-herein the term "halo" or "halogen" refers to bromo, chloro, fluoro or iodo.

As used herein the term "haloalkyl" refers to alkyl groups as defined above substituted with one or more of the same or different halo groups at one or more carbon atom. Examples of haloalkyl groups include trifluoromethyl, dichloroethyl, fluoropropyl and the like.

As used herein the term "carboxyl" or "carboxy" refers to aradical of the formula —COOH.

As used herein the term "carboxyl ester" refers to a radical of the formula —COOR$^{23}$ wherein $R^{23}$ is selected from the group consisting of H, alkyl, aralkyl or aryl as defined above.

As used herein the term "carboxyl derivative" refers to a radical of the formula

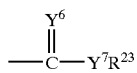

2 wherein $Y^6$ and $Y^7$ are independently selected from the group consisting of O, N or S and $R^{23}$ is selected from the group consisting of H, alkyl, araikyl and aryl as defined above.

As used herein the term "amino" is represented by a radical of the formula —$NH_2$.

As used herein the term "alkylsulfonyl" or "alkylsulfone" refers to a radical of the

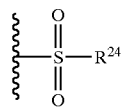

wherein $R^{24}$ is alkyl as defined above.

As used herein the term "alkylthio" refers to a radical of the formula —$SR^{24}$ wherein $R^{24}$ is alkyl as defined above.

As used herein the term "sulfonic acid" refers to a radical of the

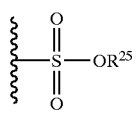

wherein $R^{25}$ is alkyl as defined above.

As used herein the term "sulfonamide" or "sulfonamido" refers to a radical

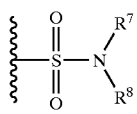

wherein $R^7$ and $R^8$ are as defined above.

As used herein the term "fused aryl" refers to an aromatic ring such as the aryl groups defined above fused to one or more phenyl rings. Embraced by the term "fused aryl" is the radical naphthyl and the like.

As used herein the terms "monocyclic heterocycle" or "monocyclic heterocyclic" refer to a monocyclic ring containing from 4 to about 12 atoms, and more preferably from 5 to about 10 atoms, wherein 1 to 3 of the atoms are heteroatoms selected from the group consisting of oxygen, nitrogen and sulfur with the understanding that if two or more different heteroatoms are present at least one of the heteroatoms must be nitrogen. Representative of such monocyclic heterocycles are imidazole, furan, pyridine, oxazole, pyran, triazole, thiophene, pyrazole, thiazole, thiadiazole, and the like.

As used herein the term "fused monocyclic heterocycle" refers to a monocyclic heterocycle as defined above with a benzene fused thereto. Examples of such fused monocyclic heterocycles include benzofuran, benzopyran, benzodioxole, benzothiazole, benzothiophene, benzimidazole and the like.

As used herein the term "methyienedioxy" refers to the radical

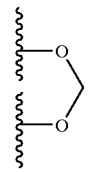

and the term "ethylenedioxy" refers to the radical

As used herein the term "4–12 membered dinitrogen containing heterocycle refers to a radical of the formula

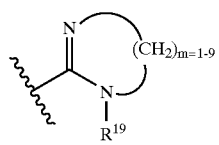

wherein m is 1 or 2 and $R^{19}$ is H, alkyl, aryl, or aralkyl and more preferably refers to 4–9 membered ring and includes rings such as imidazoline.

As used herein ihe term "5-mebered optionally substitited heteroaromatic ring" includes for example a radical of the formula

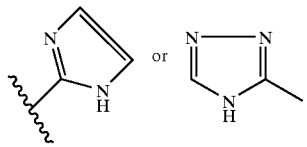

and "5-membered heteroaromatic ring fused with a phenyl" refers to such a "5-membered heteroaromatic ring" with a phenyl fused thereto. Representative of such 5-membered heteroaromatic rings fused with a phenyl is benzimidazole.

As used herein the term "bicycloalkyl" refers to a bicyclic hydrocarbon radical containing 6 to about 12 carbon atoms which is saturated or partially unsaturated.

As used herein the term "acyl" refers to a radical of the formula

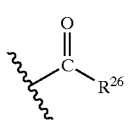

3 wherein $R^{26}$ is alkyl, alkenyl, alkynyl, aryl or aralkyl and optionally substituted thereon as defined above. Encompassed by such radical are the groups acetyl, benzoyl and the like.

As used herein the term "thio" refers to a radical of the formula

As used herein the term "sulfonyl" refers to a radical of the formula

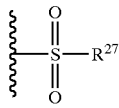

wherein $R^{27}$ is alkyl, aryl or aralkyl as defined above.

As used herein the term "haloalkylthio" refers to a radical of the formula —S—$R^{28}$ wherein $R^{28}$ is haloalkyl as defined above.

As used herein the term "aryloxy" refers to a radical of the formula

wherein $R^{29}$ is aryl as defined above.

As used herein the term "acylamino" refers to a radical of the formula

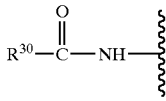

wherein $R^{30}$ is alkyl, aralkyl or aryl as defined above.

As used herein the term "amido" refers to a radical of the formula

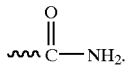

As used herein the term "alkylamino" refers to a radical of the formula —$NHR^{32}$ wherein $R^{32}$ is alkyl as defined above.

As used herein the term "dialkylamino" refers to a radical of the formula —$NR^{33}R^{34}$ wherein $R^{33}$ and $R^{34}$ are the same or different alkyl groups as defined above.

As used herein the term "trifluoromethyl" refers to a radical of the formula

As used herein the term "trifluoroalkoxy" refers to a radical of the formula

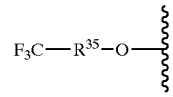

wherein $R^{35}$ is a bond or an alkylene as defined above.

As used herein the term "alkylaminosulfonyl" or "aminosulfonyl" refers to a radical of the formula

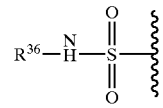

wherein $R^{36}$ is alkyl as defined above.

As used herein the term "alkylsulfonylamino" or ""alkylsulfonamide" refers to a radical of the formula

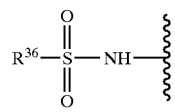

wherein $R^{36}$ is alkyl as defined above.

As used herein the term "trifluoromethylthio" refers to a radical of the formula

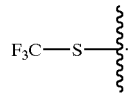

As used herein the term "trifluoromethylsulfonyl" refers to a radical of the formula

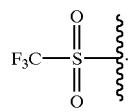

As used herein the term "4–12 membered mono-nitrogen containing monocyclic or bicyclic ring" refers to a saturated or partially unsaturated monocyclic or bicyclic ring of 4–12 atoms and more preferably a ring of 4–9 atoms wherein one atom is nitrogen. Such rings may optionally contain additional heteroatoms selected from nitrogen, oxygen or sulfur. Included within this group are morpholine, piperidine, piperazine, thiomorpholine, pyrrolidine, proline, azacycloheptene and the like.

As used herein the term "benzyl" refers to the radical

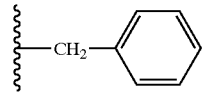

As used herein the term "phenethyl" refers to the radical

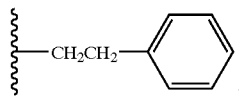

As used herein the term "4–12 membered mono-nitrogen containing monosulfur or monooxygen containing heterocyclic ring" refers to a ring consisting of 4 to 12 atoms and more preferably 4 to 9 atoms wherein at least one atom is a nitrogen and at least one atom is oxygen or sulfur. Encompassed within this definition are rings such as thiazoline and the like.

As used herein the term "arylsulfonyl" or "arylsulfone" refers to a radical of the formula

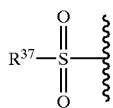

wherein $R^{37}$ is aryl as defined above.

As used herein the terms "alkylsulfoxide" or "arylsulfoxide" refer to radicals of the formula

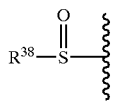

wherein $R^{38}$ is, respectively, alkyl or aryl as defined above.

As used herein the term "arylthio" refers to a radical of the formula

wherein $R^{42}$ is aryl as defined above.

As used herein the term "monocyclic heterocycle thio" refers to a radical of the formula

wherein $R^{43}$ is a monocyclic heterocycle radical as defined above.

As used herein the terms "monocyclic heterocycle sulfoxide" and "monocyclic heterocycle sulfone" refer, respectively, to radicals

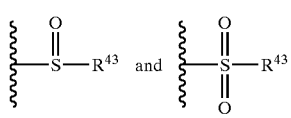

wherein $R^{43}$ is a monocyclic heterocycle radical as defined above.

As used herein the term "alkylcarbonyl" refers to a radical of the formula

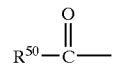

wherein $R^{50}$ is alkyl as defined above.

As used herein the term "arylcarbonyl" refers to a radical of the formula

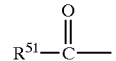

wherein $R^{51}$ is aryl as defined above.

As used herein the term "alkoxycarbonyl" refers to a radical of the formula

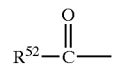

wherein $R^{52}$ is alkoxy as defined above.

As used herein the term "aryloxycarbonyl" refers to a radical of the formula

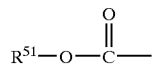

wherein $R^{51}$ is aryl as defined above.

As used herein the term "haloalkylcarbonyl" refers to a radical of the formula

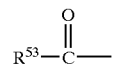

wherein $R^{53}$ is haloalkyl as defined above.

As used herein the term "haloalkoxycarbonyl" refers to a radical of the formula

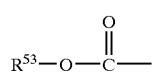

4 wherein $R^{53}$ is haloalkyl as defined above.

As used herein the term "alkylthiocarbonyl" refers to a radical of the formula

wherein $R^{50}$ is alkyl as defined above.

As used herein the term "arylthiocarbonyl" refers to a radical of the formula

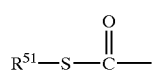

wherein $R^{51}$ is aryl as defined above.

As used herein the term "acyloxymethoxycarbonyl" refers to a radical of the formula

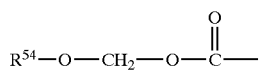

wherein $R^{54}$ is acyl as defined above.

As used herein the term "arylamino" refers to a radical of the formula $R^{51}$—NH— wherein $R^{51}$ is aryl as defined above.

As used herein the term "acyloxy" refers to a radical of the formula $R^{55}$—O— wherein $R^{55}$ is acyl as defined above.

As used herein the term "alkenylalkyl" refers to a radical of the formula $R^{50}$—$R^{57}$— wherein $R^{50}$ is an alkenyl as defined above and $R^{57}$ is alkylene as defined above.

As used herein the term "alkenylene" refers to a linear hydrocarbon radical of 1 to about 8 carbon atoms containing at least one double bond.

As used herein the term "alkoxyalkyl" refers to a radical of the formula $R^{56}$—$R^{57}$— wherein $R^{56}$ is alkoxy as defined above and $R^{57}$ is alkylene as defined above.

As used herein the term "alkynylalkyl" refers to a radical of the formula $R^{59}$—$R^{60}$— wherein $R^{59}$ is alkynyl as defined as above and $R^{60}$ is alkylene as defined as above.

As used herein the term "alkynylene" refers to divalent alkynyl radicals of 1 to about 6 carbon atoms.

As used herein the term "allyl" refers of a radical of the formula —$CH_2CH=CH_2$.

As used herein the term "aminoalkyl" refers to a radical of the formula $H_2N$—$R^{61}$ wherein $R^{61}$ is alkylene as defined above.

As used herein the term "benzoyl" refers to the aryl radical $C_6H_5$—CO—.

As used herein the term "carboxamide" or "carboxamido" refer to a radical of the formula —CO—$NH_2$.

As used herein the term "carboxyalkyl" refers to a radical HOOC—$R^{62}$— wherein $R^{62}$ is alkylene as defined as above.

As used herein the term "carboxylic acid" refers to the radical —COOH.

As used herein the term "ether" refers to a radical of the formula $R^{63}$—O— wherein $R^{63}$ is selected from the group consisting of alkyl, aryl and heteroaryl.

As used herein the term "haloalkylsulfonyl" refers to a radical of the formula

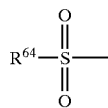

wherein the $R^{64}$ is haloalkyl as defined above.

As used herein the term "heteroaryl" refers to an aryl radical contain at least one heteroatom.

As used herein the term "hydroxyalkyl" refers to a radical of the formula HO—$R^{65}$— wherein $R^{65}$ is alkylene as defined above.

As used herein the term "keto" refers to a carbonyl group joined to 2 carbon atoms.

As used herein the term "lactone" refers to an anhydro cyclic ester produced by intramolecular condensation of a hydroxy acid with the elimination of water.

As used herein the term "olefin" refers to an unsaturated hydrocarbon radical of the type $C_nH_{2n}$.

As used herein the term "sulfone" refers to a radical of the formula $R^{66}$—$SO_2$—.

As used herein the term "thioalkyl" refers to a radical of the formula $R^{77}$—S— wherein $R^{77}$ is alkyl as defined above.

As used herein the term "thioether" refers to a radical of the formula $R^{78}$—S— wherein $R^{78}$ is alkyl, aryl or heteroaryl.

As used herein the term "trifluoroalkyl" refers to an alkyl radical as defined above substituted with three halo radicals as defined above.

The term "composition" as used herein means a product which results from the mixing or combining of more than one element or ingredient.

The term "pharmaceutically acceptable carrier", as used herein means a pharmaceutically acceptable material, composition or vehicle, such as a liquid or solid filler, diluent, excipient, solvent or encapsulating material, involved in carrying or transporting a chemical agent.

The term "therapeutically effective amount" shall mean that amount of drug or pharmaceutical agent that will elicit the biological or medical response of a tissue, system or animal that is being sought by a researcher or clinician.

The following is a list of abbreviations and the corresponding meanings as used interchangeably herein:

$^1$H-NMR=proton nuclear magnetic resonance
AcOH=acetic acid
BOC=tert-butoxycarbonyl
BuLi=butyl lithium
Cat.=catalytic amount
$CH_2Cl_2$=dichloromethane
$CH_3CN$=acetonitrile
$CH_3I$=iodomethane
CHN analysis=carbon/hydrogen/nitrogen elemental analysis
CHNCl analysis=carbon/hydrogen/nitrogen/chlorine elemental analysis
CHNS analysis=carbon/hydrogen/nitrogenlsulfur elemental analysis
DEAD=diethylazodicarboxylate
DIAD=diisopropylazodicarboxylate
DI water=deionized water
DMA=N,N-dimethylacetamide
DMAC=N,N-dimethylacetamide
DMF=N,N-dimethylformamide
EDC=1-(3-dimethylaminopropyl)-3-ethylcarbodiimide hydrochloride
Et=ethyl
$Et_2O$=diethyl ether
$Et_3N$=triethylamine
EtOAc=ethyl acetate
EtOH=ethanol
FAB MS=fast atom bombardment mass spectroscopy
g=gram(s)
HOBT=1-hydroxybenzotriazole hydrate
HPLC=high performance liquid chromatography
i-Pr=iso propyl
i-Prop=iso propyl
$K_2CO_3$=potassium carbonate
$KMnO_4$=potassium permanganate
KOH=potassium hydroxide
KSCN=potassium thiocyanate
L=Liter
LiOH=lithium hydroxide
Me=methyl
MeOH=methanol
mg=milligram
$MgSO_4$=magnesium sulfate ml=milliliter
mL=milliliter
MS=mass spectroscopy
NaH—sodium hydride
$NaHCO_3$=sodium bicarbonate
NaOH=sodium hydroxide
NaOMe=sodium methoxide
$NH_4^+HCO_2^-$=ammonium formate
NMR=nuclear magnetic resonance
Pd=palladium
Pd/C=palladium on carbon
Ph=phenyl
Pt=platinum
Pt/C=platinum on carbon
RPHPLC=reverse phase high performance liquid chromatography
RT=room temperature
t-BOC=tert-butoxycarbonyl
TFA=trifluoroacetic acid
THF=tetrahydrofuran
TLC—thin layer chromatography
TMS=trimethylsilyl
Δ=heating the reaction mixture The compounds as shown above can exist in various isomeric forms and all such isomeric forms are meant to be included. Tautomeric forms are also included as well as pharmaceutically acceptable salts of such isomers and tautomers.

In the structures and formulas herein, a bond drawn across a bond of a ring can be to any available atom on the ring.

The term "pharmaceutically acceptable salt" refers to a salt prepared by contacting a compound of Formula I or II with an acid whose anion is generally considered suitable for human consumption. For use in medicine, the salts of the compounds of this invention are non-toxic "pharmnaceutically acceptable salts." Salts encompassed within the term "pharmaceutically acceptable salts" refer to non-toxic salts of the compounds of this invention which are generally prepared by reacting the free base with a suitable organic or inorganic acid. Representative salts include the following: acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylgucamine ammonium salt, oleate, oxalate, pamoate (embonate), palmitate, pantothenate, phosphate/disphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof may include alkali metal salts, e.g., sodium or potassium salts, alkaline earth metal salts, e.g., calcium or magnesium salts; and salts formed with suitable organic ligands, e.g., quaternary ammonium salts. All of the pharmacologically acceptable salts may be prepared by conventional means. (See Berge et al., *J Pharm. Sci.*, 66(1), 1–19 (1977) for additional examples of pharmaceutically acceptable salts.)

The compounds of the present invention can have chiral centers and occur as racemates, racemic mixtures, diastereomeric mixtures, and as individual diastereomers or enantiomers, with all isomeric forms included in the present invention. Therefore, where a compound is chiral, the separate enantiomers or diastereomers, substantially free of the other, are included within the scope of the present invention; further included are all mixtures of the enantiomers or diastereomers. Also included within the scope of the invention are polymorphs, or hydrates or other modifiers of the compounds of invention.

The present invention includes within its scope prodrugs of the compounds of this invention. In general, such prodrugs will be functional derivatives of the compounds of this invention which are readily convertible in vivo into the required compound. For example, prodrugs of a carboxylic acid may include an ester, an amide, an ortho-ester, or heterocycles such as tettazole. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

For the selective inhibition or antagonism of $\alpha_v\beta_3$ and/or $\alpha_v\beta_5$ integrins, compounds of the present invention may be administered orally, parenterally, or by inhalation spray, or topically in unit dosage formulations containing conventional pharmaceutically acceptable carriers, adjuvants and vehicles. The term parenteral as used herein includes, for example, subcutaneous, intravenous, intramuscular, intrasternal, transmuscular infusion techniques or intraperitonally.

The compounds of the present invention are administered by any suitable route in the form of a pharmaceutical composition adapted to such a route, and in a dose effective for the treatment intended. Therapeutically effective doses of the compounds required to prevent or arrest the progress of or to treat the medical condition are readily ascertained by one of ordinary skill in the art using preclinical and clinical approaches familiar to the medicinal arts.

Accordingly, the present invention provides a method of treating conditions mediated by selectively inhibiting or antagonizing the $\alpha_v\beta_3$ and/or $\alpha_v\beta_5$ cell surface receptor which method comprises administering a therapeutically effective amount of a compound selected from the class of compounds depicted in the above formulas, wherein one or more compound is administered in association with one or more non-toxic, pharmaceutically acceptable carriers and/or diluents and/or adjuvants (collectively referred to herein as "carrier" materials) and if desired other active ingredients. The present invention also provides a method for selective inhibition of the $\alpha_v\beta_3$ and/or $\alpha_v\beta_5$ cell surface receptors with a reduced $\alpha_v\beta_6$ inhibition. Another aspect of the invention provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating retinopathy including macular degeneration and diabetic retinopathy, inhibiting arthritis, psoriasis and periodontal disease, and inhibiting smooth muscle cell migration including restenosis.

In another embodiment, the present invention provides a method for selective antagonism of the $\alpha_v\beta_3$ and/or $\alpha_v\beta_5$ cell surface receptors over $\alpha_{IIb}\beta_3$ and in a further embodiment, also over the $\alpha_v\beta_6$ integrin receptor. Evidence of the toxicity of $\beta_6$ integrin antagonism indicates that it may be beneficial to spare antagonism of $\beta_6$ when designing $\alpha_v\beta_3$ antagonists, in addition to sparing $\alpha_{IIb}\beta_3$. Selectivite inhibition refers to a selectivity ratio of at least 10, more preferably 50, and even more preferably of at least 100. Selectivity ratio refers to the selectivity of the $IC_{50}$ of $\alpha_v\beta_6$ or $\alpha_{IIb}\beta_3$ over the selectivity of the $IC_{50}$ of $\beta_3$.

Based upon standard laboratory experimental techniques and procedures well known and appreciated by those skilled in the art, as well as comparisons with compounds of known usefulness, the compounds of Formula I or II can be used in the treatment of patients suffering from the above pathological conditions. One skilled in the art will recognize that selection of the most appropriate compound of the invention is within the ability of one with ordinary skill in the art and will depend on a variety of factors including assessment of results obtained in standard assay and animal models.

Treatment of a patient afflicted with one of the pathological conditions comprises administering to such a patient an amount of compound of the Formula I which is therapeutically effective in controlling the condition or in prolonging the survivability of the patient beyond that expected in the absence of such treatment. As used herein, the term "inhibition" of the condition refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

As stated previously, the compounds of the invention can be used in a variety of biological, prophylactic or therapeutic areas. It is contemplated that these compounds are useful in prevention or treatment of any disease state or condition wherein the $\alpha_v\beta_3$ and/or $\alpha_v\beta_5$ integrin plays a role.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 1.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100, 200 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenous doses will range from about 0.1 to about 10 mg/kg/minute during a constant rate infusion. Compounds of the present invention may be administered in a single daily dose, or the total daily dosage may be administered in divided doses of two, three or four times daily. Furthermore, compounds of the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration may be continuous rather than intermittant throughout the dosage regiment.

For administration to a mammal in need of such treatment, the compounds in a therapeutically effective amount are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions useful in the present invention may be subjected to conventional pharmaceutical operations such as sterilization and/or may contain conventional pharmaceutical adjuvants such as preservatives, stabilizers, wetting agents, emulsifiers, buffers, etc.

The following Schemes are intended to be merely illustrative of the present invention, and not limiting thereof in either scope or spirit. Those skilled in the art will readily understand that known variations of the conditions and processes described in the Schemes can be used to make the embodiments of the invention.

Scheme 1
Preparation of S-3-aminobutyrolactone hydrochloride salt

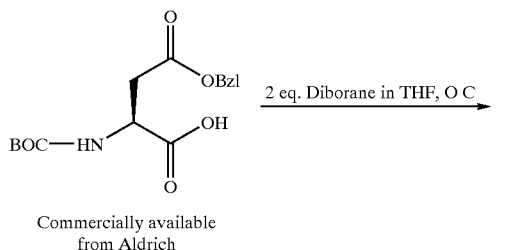

Commercially available from Aldrich

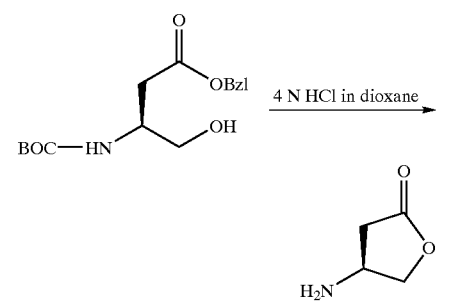

Solid, crystallizes from reaction mixture)

Scheme 2
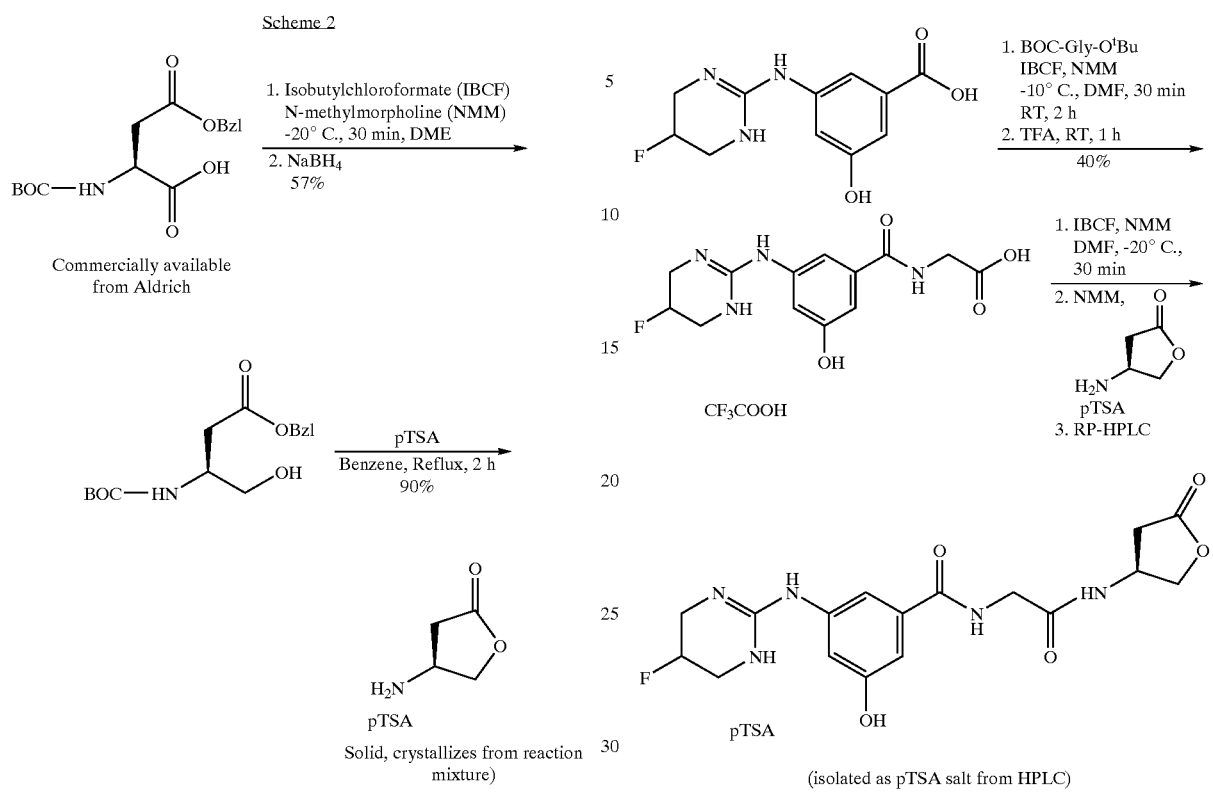
SCHEME 3
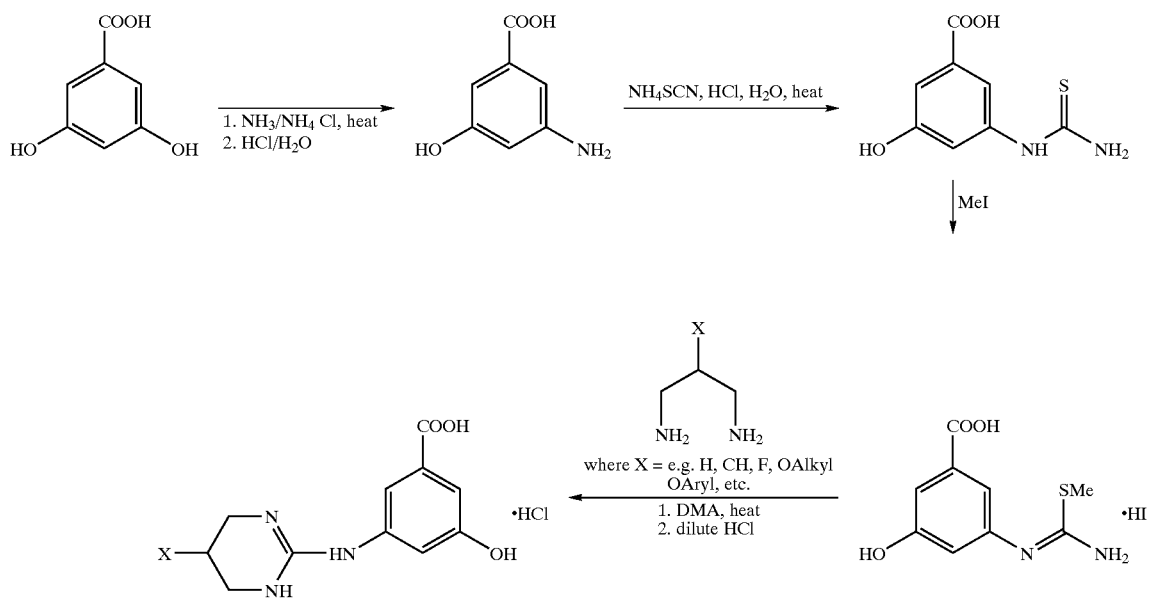

Scheme 4

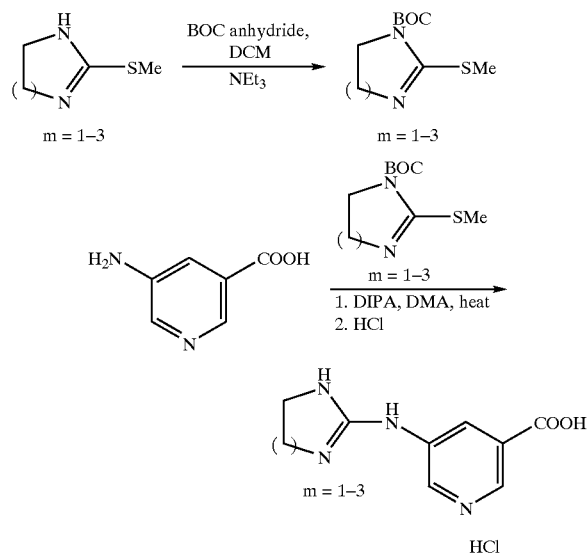

Scheme 5

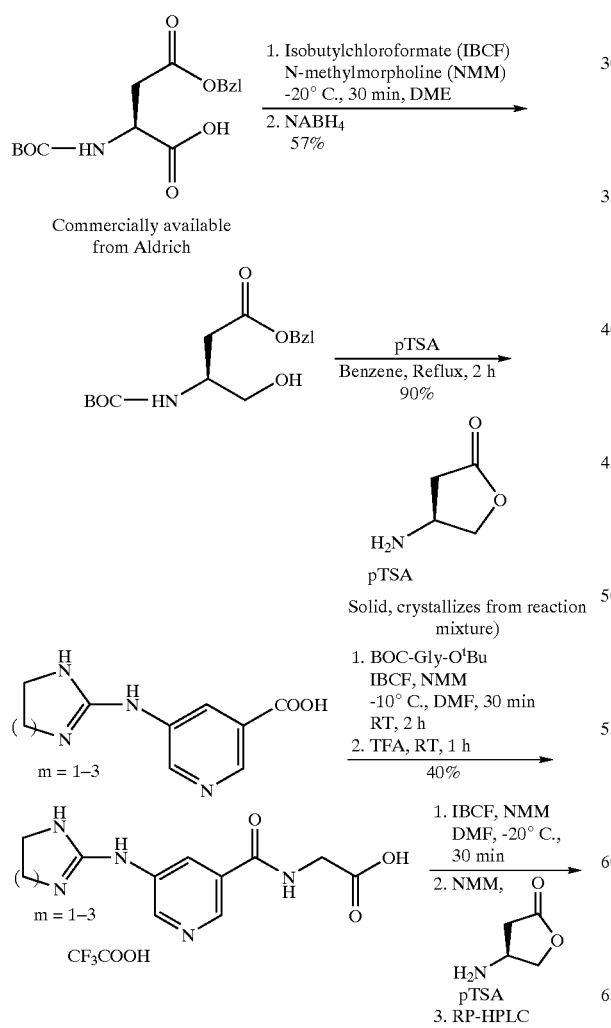

Scheme 6

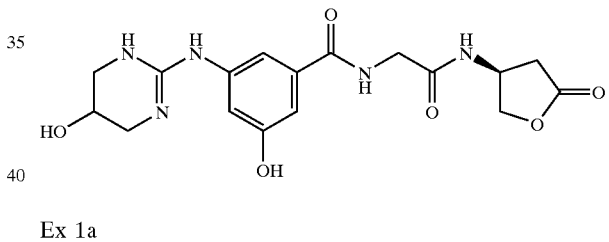

The following Examples are intended to be illustrative and not intended to limit the scope of the invention.

EXAMPLE 1

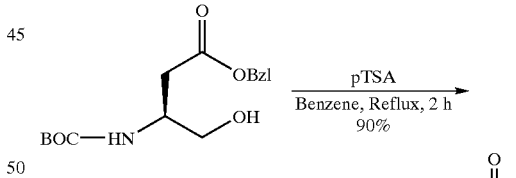

Ex 1a

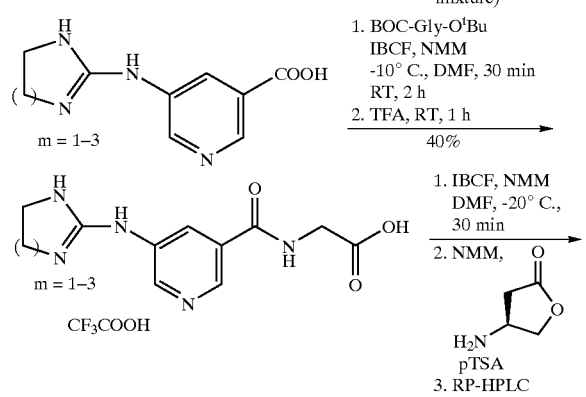

Synthesis of 3-amino-5-oxo-3S-furan hydrochloride

A solution of the Boc-aspartimol-γ-benzylester (0.5 g, Tetrahedron Lett. 32, (7), 923, 1991) in dry benzene (10.0 mL) containing p-toluenesulfonic acid (0.32 g) was heated to reflux for 1.5 h. under anhydrous conditions. The reaction mixture was cooled, diluted with ether and filtered the precipitate. It was washed with ether, and dried to give 0.38 g of the desired lactone as its p-toluenesufonate salt:

$^1$H-NMR (DMSO-d$_6$) δ 8.14 (br, 2H), 7.46 (d, 2H, J=8.0 Hz), 7.09 (d, 2H, J=8.0 Hz), 4.46 (m, 1H), 4.24 (m, 1H), 4.19(m, 1H), 2.96 (dd, 1H), 2.47 (dd, 2H), 2.2 (, 3H); MS: m/z 102 (MH$^+$)

Ex 1b

Alternate preparation of of 3-amino-5-oxo-3S-furan hydrochloride.

N-tBoc-L-aspartic acid, β-benzyl ester (10.0 mmole) was dissolved in 10 mL of tetrahydrofuran (THF) and added drop-wise over a period of 30 min to a 0° C. solution of BH$_3$-THF (20 mL, 20.0 mmole) under argon. After the mixture was stirred for an additional 1–2 hr at 0° C., the reaction was quenched by drop-wise addition of 10% acetic acid in methanol and the solvent evaporated. The oil residue was dissolved in ethyl acetate and extracted with 1N HCl, water, and 1M NH$_4$HCO$_3$. The ethyl acetate layer was dried (Na$_2$SO$_4$) and volatiles evaporated to give an oil that could be crystalized from isopropanol/hexane (mp 56–57° C.):$^1$H NMR (CDCL$_3$) δ 1.45 (s, 9H), 2.65 (d, 2H), 3.68 (d, 2H), 5.12 (s, 2H), 5.25 (m, 1H), 7.35 (m, 5H).

The resulting 3-N-tBoc-amino-4-hydroxy-butyric acid benzyl ester (20 g. 64 mmole) was stirred in 200 mL dichloromethane at room temperature for 16 hr in the presence of a catalytic amount of camphor sulfonic acid. Solvent was removed in vacuo and the crude product purified by flash chromatography (Merck 60 silica gel, ethyl acetate/hexane/1% triethylamine). The N-tBoc-3-aminolactone was isolated as a white solid (5.4 g).

The 3-N-tBoc-aminolactone (5.0 g, 25 mmole) isolate was dissolved in 20 mL 4N HCl/dioxane. After 45 minutes at 25° C., 10 mL of 4N HCl/dioxane was added and after 1 hr the excess HCl was removed in vacuo. The resulting solution. deposited white crystals upon standing. These were filtered and dried to give 2.9 g of the desired product as the hydrochloride salt. $^1$H NMR (d$_6$ DMSO) δ 2.55 (dd, J$_1$=18.3 Hz, J$_2$=2.5 Hz), 3.0 (dd, 1H, J$_1$=8.5 Hz, J$_2$=18.3 Hz), 4.1 (m, 1H), 4.35 (dd, 1H, J$_1$=10.5 Hz, J$_2$=2.7 Hz), 4.5 (dd, 1H, J$_1$=10.5 Hz, J$_2$=6.5 Hz); MS (FAB) 102.1 (M+H).

Ex 1c

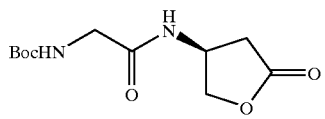

3-amino-5-oxo-3S-furan hydrochloride (2.9 g, 21 mmol) was dissolved in DMF (123 mL) and cooled to 0° C. under a nitrogen atmosphere. N-Boc-Gly-OSu (5.4 g, 20 mmol) was added, followed by 4-methylmorpholine (2.3 mL, 21 mmol). After the solution was stirred 18 hours, it was diluted with brine and extracted twice with EtOAc. The combined organic layers were washed with H$_2$O, dried (Na$_2$SO$_4$), filtered, and concentrated in vacuo. The residue was purified by chromatography on silica gel (eluent: EtOAc) to give a colorless oil (4.7 g, 87%). $^1$H NMR (CDCl$_3$) δ 1.46 (s, 9H), 2.51 (dd, 1H), 2.89 (dd, 1H), 3.82 (s, 2H), 4.25 (dd, 1H), 4.54 (dd, 1H), 4.72 (m, 1H).

Ex 1d

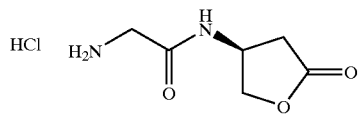

The colorless oil from Ex 1c (3.2 g, 12.4 mmol) was dissolved in 4N HCl dioxane (30 mL). After stirring 2.5 hours at ambient temperature, the excess HCl was removed in vacuo. The white solid material was filtered and dried (2.4 g, 98%). $^1$H NMR (CD$_3$OD) δ 2.51 (dd, 1H), 2.92 (dd, 1H), 3.68 (s, 2H), 4.28 (dd, 1H), 4.57 (dd, 1H), 4.63 (m, 1H). EI-MS m/z 159 (MH$^+$).

Ex 1e

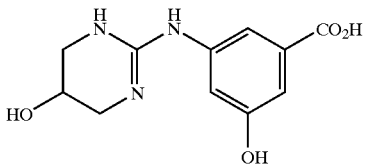

Acid A

The amine hydrochloride from Ex 1d (950 mg, 4.9 mmol) and Acid A (1.4 g, 4.9 mmol, prepared according to U.S. Pat. No. 6,013,651, Example H) were combined and slurried in DMF/CH$_2$Cl$_2$ (12 mL, 1:1) at ambient temperature under a nitrogen atmosphere. 1,3-Diisopropylcarbodiimide (0.9 mL, 5.9 mmoL) was added, followed by 4-methylmorpholine (0.5 mL, 4.9 mmol). After stirring 18 hours, the solution was filtered through a pad of Celite and the filtrate concentrated in vacuo. The resulting oil was purified by reverse-phase HPLC (H$_2$O/CH$_3$CN) to afford the title compound as a white solid (671 mg, 20%). $^1$H NMR (DMSO-d$_6$) δ 2.37 (dd, 1H), 2.90 (dd, 1H), 3.16 (dd, 2H), 3.35 (dd, 2H), 3.82 (d, 2H), 4.09 (m, 2H), 4.48 (m, 2H), 6.75 (t, 1H) 7.11 (t, 1H), 7.14 (m, 1H), 8.18 (s, 2H), 8.54 (d, 1H), 8.63 (t, 1H), 9.71 (s, 1H). EI-MS m/z 392 (MH$^+$). Anal. Calcd for C$_{17}$H$_{21}$N$_5$O$_6$+2.5 TFA+0.5 H$_2$O: C, 38.55; H, 3.60. Found: C, 38.55; H, 3.87.

EXAMPLE 2

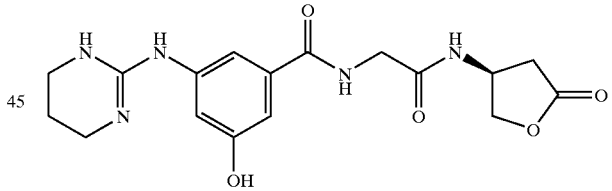

Ex 2a

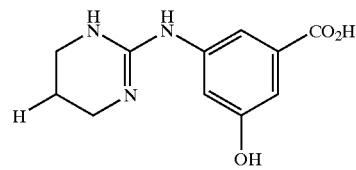

Acid B

The amine hydrochloride from Ex 1d (950 mg, 4.9 mmol) and Acid B (1.3 g, 4.9 mmol, prepared using similar procedure according to U.S. Pat. No. 6,013,651, Example H) were combined and slurried in DMF/CH$_2$Cl$_2$ (12 mL, 1:1) at ambient temperature under a nitrogen atmosphere. 1,3-Diisopropylcarbodiimide (0.9 mL, 5.9 mmoL) was added, followed by 4-methylmorpholine (0.5 mL, 4.9 mmol). After stirring 18 hours, the solution was filtered through a pad of Celite and the filtrate concentrated in vacuo. The resulting oil was purified by reverse-phase HPLC (H₂O/CH₃CN) to afford the title compound as a light yellow solid (760 mg, 25%). ¹H NMR (DMSO-d₆) δ 1.89 (m, 2H), 2.37 (dd, 1H), 2.89 (dd, 1H), 3.16 (dd, 2H), 3.28 (m, 4H), 3.84 (d, 2H), 4.09 (m, 1H), 4.48 (m, 2H), 6.75 (t, 1H) 7.11 (t, 1H), 7.14 (m, 1H), 8.32 (s, 2H), 8.54 (d, 1H), 8.63 (t, 1H), 9.89 (s, 1H). EI-MS m/z 376 (MH³⁰ ). Anal. Calcd for $C_{17}H_{21}N_5O_5$+2 TFA+0.3 H₂O: C, 41.43; H, 3.91; N, 11.50. Found: C, 41.21; H, 4.07; N, 11.74.

EXAMPLE 3

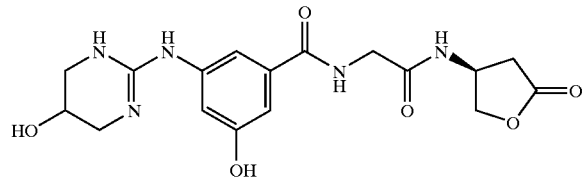

Ex 3a

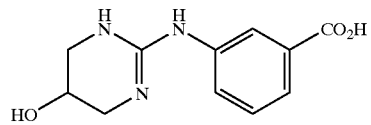

Acid C

The amine hydrochloride from Ex 1d (950 mg, 4.9 mmol) and Acid C (1.0 g, 3.7 mmol, prepared using similar procedure according to U.S. Pat. No. 6,013,651, Example H) were combined and slurried in DMF/CH₂Cl₂ (12 mL, 1:1) at ambient temperature under a nitrogen atmosphere. 1,3-Diisopropylcarbodiimide (0.9 mL, 5.9 mmoL) was added, followed by 4-methylmorpholine (0.5 mL, 4.9 mmol). After stirring 18 hours, the solution was filtered through a pad of Celite and the filtrate concentrated in vacuo. The resulting oil was purified by reverse-phase HPLC (H₂O/CH₃CN) to afford the title compound as a light yellow solid (150 mg, 7%). ¹H NMR (DMSO-d₆) δ 2.39 (dd, 1H), 2.90 (dd, 1H), 3.17 (dd, 2H), 3.38 (dd, 2H), 3.87 (d, 2H), 4.10 (m, 2H), 4.48 (m, 2H), 7.36 (m, 1H), 7.52 (t, 1H), 7.70 (m, 1H), 7.75 (m, 1H), 8.38 (s, 2H), 8.62 (d, 1H), 8.83 (t, 1H), 10.08 (s, 1H). EI-MS m/z 376 (MH⁺). Anal. Calcd for $C_{17}H_{21}N_5O_5$+2 TFA+0.5 H₂O: C, 41.18; H, 3.95; N, 11.44. Found: C, 40.86; H, 3.90; N, 11.83.

EXAMPLE 4

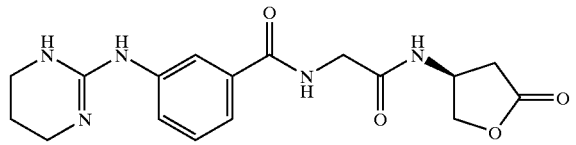

Ex 4a

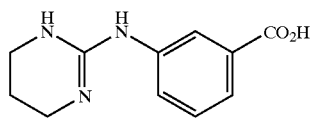

Acid D

The amine hydrochloride from Ex 1d (950 mg, 4.9 mmol) and Acid D (899 g, 3.5 mmol, prepared according to U.S. Pat. No. 6,028,223, Example 236, Step B) were combined and slurried in DMF/CH₂Cl₂ (12 mL, 1:1) at ambient temperature under a nitrogen atmosphere. 1,3-Diisopropylcarbodiimide (0.9 mL, 5.9 mmoL) was added, followed by 4-methylmorpholine (0.5 mL, 4.9 mmol). After stirring 18 hours, the solution was filtered through a pad of Celite and the filtrate concentrated in vacuo. The resulting oil was purified by reverse-phase HPLC (H₂O/CH₃CN) to afford the title compound as a light yellow solid (600 mg, 30%). ¹H NMR (DMSO-d₆) d 1.89 (m, 2H), 2.39 (dd, 1H), 2.89 (dd, 1H), 3.28 (m, 4H), 3.84 (d, 2H), 4.09 (m, 1H), 4.48 (m, 2H), 7.37 (m, 1H), 7.53 (t, 1H), 7.70 (m, 1H), 7.74 (m, 1H), 8.29 (s, 2H), 8.61 (d, 1H), 8.83 (t, 1H), 9.93 (s, 1H). EI-MS m/z 360 (MH⁺). Anal. Calcd for $C_{17}H_{21}N_5O_4$+1 TFA+1 H₂O+1 DMF: C, 46.81; H, 5.54; N, 14.89. Found: C, 46.69; H, 5.21; N, 14.69.

EXAMPLE 5

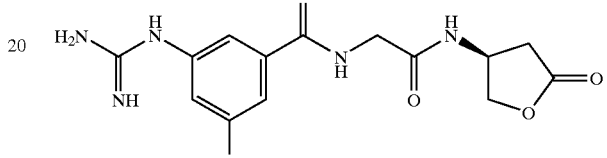

Ex 5a

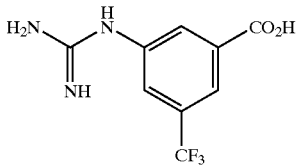

Acid E

The amine hydrochloride from Ex 1c (950 mg, 4.9 mmol) and Acid B (1.0 g, 3.5 mmol, prepared using similar procedure according to U.S. Pat. No. 6,028,223, Example38) were combined and slurried in DMF/CH₂Cl₂ (12 mL, 1:1) at ambient temperature under a nitrogen atmosphere. 1,3-Diisopropylcarbodiimide (0.9 mL, 5.9 mmoL) was added, followed by 4-methylmorpholine (0.5 mL, 4.9 mmol). After stirring 18 hours, the solution was filtered through a pad of Celite and the filtrate concentrated in vacuo. The resulting oil was purified by reverse-phase HPLC (H₂O/CH₃CN) to afford the title compound as a light yellow solid (600 mg, 30%). ¹H NMR (DMSO-d₆) d 1.89 (m, 2H), 2.39 (dd, 1H), 2.89 (dd, 1H), 3.28 (m, 4H), 3.84 (d, 2H), 4.09 (m, 1H), 4.48 (m, 2H), 7.37 (m, 1H), 7.53 (t, 1H), 7.70 (m, 1H), 7.74 (m, 1H), 8.29 (s, 2H), 8.61 (d, 1H), 8.83 (t, 1H), 9.93 (s, 1H). EI-MS m/z 360 (MH⁺). Anal. Calcd for $C_{17}H_{21}N_5O_4$+1 TFA+1 H₂O+1 DMF: C, 46.81; H, 5.54; N, 14.89. Found: C, 46.69; H, 5.21; N, 14.69.

EXAMPLE 6

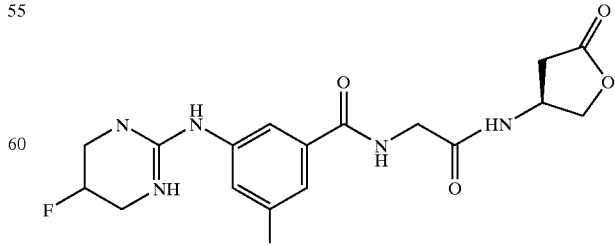

pTSA salt

Ex 6a
3-[(5-fluoro-1,4,5,6-tetrahydro-2-pyrimidinyl)amino]-5-hydroxybenzoic acid

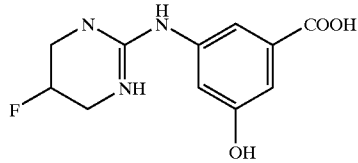

Acid F
Step A

To a solution of 1,3 diamino-2-fluoropropane (8.3 g), in DMF (100 mL), was added triethylamine (10.0 mL), followed by the addition of S-methylisothiourea (16 g) and the resulting mixture was stirred at room temperature. After 30 mins of stirring, the reaction mixture was heated to 90° C., under anhydrous conditions for 3 h, when a light brown precipitate was obtained. DMF was distilled in vacuo, residue was triturated with water, and filtered. The precipitate was washed thoroughly with water, followed by acetonitrile, and dried in a desiccator in vacuo to afford 8.0 g of 8–6 as a light brown powder. This was used as such in Step B.

Step B

To a chilled suspension of the above product (0.265 g, 0.0010 mol) in anhydrous THF (5 mL) was added HCl/dioxane (4N, 0.52 mL, 2 eqiv) and stirred cold 1 h. The solvent was removed under reduced pressure to afford the desired hydrochloride salt 8–7 after drying (0.339 g, 99%): $^1$H-NMR (CD$_3$OD) δ 7.38 (m, 1H), 7.33 (m, 1H), 5.15 (m, 1H), 3.63–3.4 (m, 4H); HR-MS m/z (MH+) calcd C11H13N3FO3 (MH+) 254.0941, found 254.0944.

Ex 6b

To a solution of Acid F (0.57 g, 0.002 mol) in DMF (5.0 mL) was added isobutylchloroformate (0.25 mL), followed by the drop-wise addition of N-methyl-morpholine (0.26 mL) and the mixture was stirred at −10° C. under an atmosphere of argon (Scheme III). After 20 min, a solution of the amine generated by the addition of N-methyl-morpholine (0.26 mL) to a solution of glycine-t-butylester hydrochloride (0.4 g, 0.0024 mol) in DMF (5.0 mL) was added and the resulting mixture was stirred at room temperature for 6 h. DMF was distilled in vacuo, and the residue was purified by reverse-phase HPLC using 10–90% acetonitrile/water at flow rate of 70 mL/min. The appropriate fractions were combined and freeze dried to obtain 0.32 g of the desired $^t$butylester as a white powder. $^1$H-NMR (CD$_3$OD) δ 7.19 (m, 1H), 7.15 (d, 1H, J=1.6 Hz), 6.82 (m, 1H), 5.20 (2t, 1H, J$_{H,F}$=44 Hz, J=2.4 Hz), 3.98 (s, 2H), 3.65–3.45 (m, 4H), and 1.47 (s, 9H), HR-MS: m/z calcd for C$_{17}$H$_{24}$N$_4$O$_4$F (MH+) 367.1782, found 367.1776.

Ex 6c

A solution of the t-butylester (0.6 g, 0.00164 mol) as prepared in Ex 6b was stirred with trifluoroacetic acid (3.0 mL) at room temperature for 1 h and concentrated to dryness under reduced pressure. The resulting product (TFA salt) was suspended in toluene (5.0 mL) and concentrated to dryness in vacuo, and dried in a desiccator for 4 h over NaOH pallets. This material was used as such in Ex 6d.

Ex 6d

The TFA salt from Ex 6c, was dissolved in dry DMF (5.0 mL), added isobutylchloroformate (0.2 mL), followed by the addition of N-methylmorpholine (0.2 mL) and stirred at −15° C. under argon atmosphere. After 30 min, the 3-amino-5-oxo-3S-furan (0.44 g, 0.0016 mol) prepared in Ex 1a, and N-methylmorpholine (0.2 mL) were added and the resulting mixture was stirred at −10° C. for an additional 30 min, and at room temperature for 2 h. The solvents were distilled in vacuo and the crude material was purified by reverse-phase HPLC using a gradient of 10–90% acetonitrile/water at flow rate of 70 mL/min. The appropriate fractions as revealed by mass spectrum of the fractions (MH+ m/z 394) were combined and freeze dried to obtain the desired lactone as its p-toluenesulfonate salt (0.31 g): $^1$H-NMR (CD$_3$OD) δ 8.04 (br, 1H), 7:68 (d, 2H, J=8.4 Hz), 7.22 (m, 2H), 7.17 (t 1H, J=2.0 Hz), 6.82 (m, 1H), 5.19 (d, 1H, J=46.4 Hz), 4.58 (m 1H), 4.52 (m 1H), 4.21 (dd, 1H, J=2.8 Hz), 3.98 (s, 2H), 3.65–3.35 (m 4H), 2.90 (dd, 1H, J=8.4 Hz), 2.47 (dd, 1H, J=3.6 Hz), 2.35 (s, 3H); HR-MS m/z calcd for C$_{17}$H$_{21}$N$_5$O$_5$F (MH$^{30}$) 394.1527, found 394.1527.

EXAMPLE 7

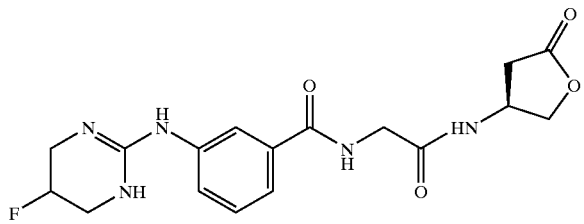

The title compound is prepared according to procedure used in the preparation of EXAMPLE 6 using the corresponding starting materials.

EXAMPLE 8

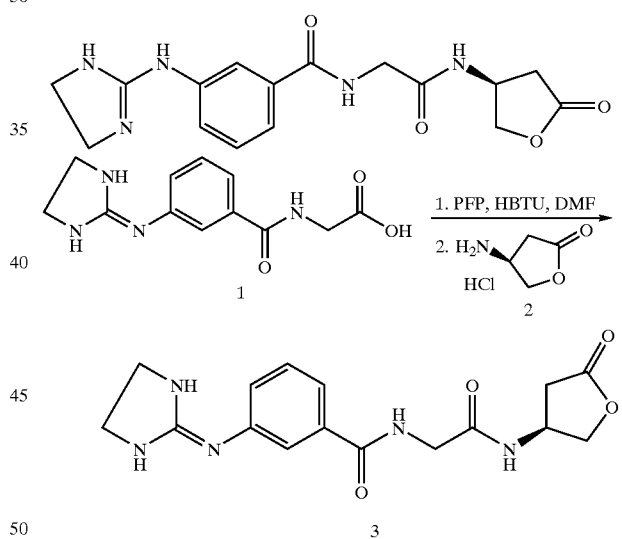

To the mixture of 1 (900 mg, 3.0 mmol, prepared using similar procedure described in EXAMPLE 6, step 6a, 6b, 6c) and pentafluorophenol (1.10 g, 6.0 mmol) in DMF (10 ml) was added O-Benzotriazole-N,N,N',N'-tetramethyl-uronium-hexafluoro-phosphate (HBTU) (1.14 g, 3.0 mmol) The mixture was stirred for two hours at room temperature. To this resulting mixture was added a solution of 2 (416 mg, 3.0 mmol) and N-methyl morpholine (303 mg, 3.0 mmol) in DMF (5.0 ml). After the mixture was stirred for 16 hours at room temperature, it was quenched with water and the solvents were allowed to evaporated under reduced pressure. The residue was purified through preparative HPLC (C-18 column, eluted with water/acetonitrile) to isolate desired product 3 (750 mg) as a white amorphous solid. $^1$HNMR (400 MHz, DMSO-d6, vs TMS) δ: 2.57(1H, dd, J=3.49, 3.57

Hz), 2.97(1H, dd, J=8.21, 8.20 Hz), 3.82(4H, s), 4.06(2H, s), 4.27(1H, dd, J=3.06, 3.27 Hz), 4.56(1H, dd, J=9.50, 9.54 Hz), 4.62(1H, m), 7.48(1H, m), 7.57(1H, m), 7.59(1H, m), 7.83(1H, m) ppm. Anal. Calcd for $C_{16}H_{19}N_5O_4 \cdot 1.2 H_2O \cdot 1.1TFA$: C, 44.23; H, 4.63; N, 14.17. Found: C, 43.95; H, 4.39; N, 14.37.

EXAMPLE 9

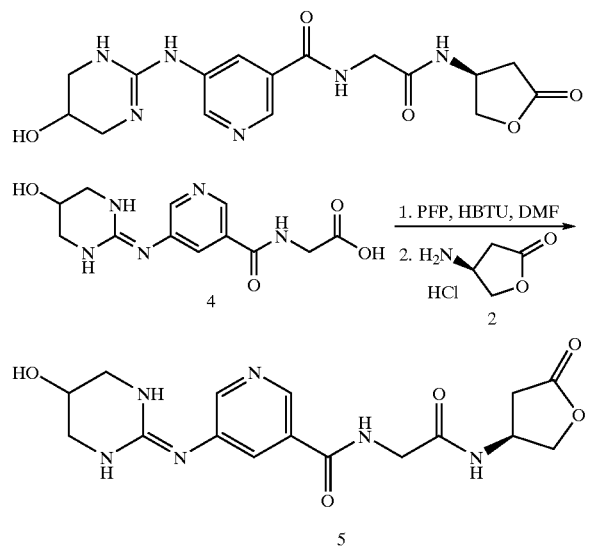

To the mixture of 4 (730 mg, 1.73 mmol) and pentafluorophenol (637 mg, 3.46 mmol) in DMF (5.0 ml) was added O-Benzotriazole-N,N,N',N'-tetramethyl-uronium-hexafluoro-phosphate (HBTU) (656 mg, 1.73 mmol). The mixture was stirred for two hours at room temperature. To this resulting mixture was added a solution of 2 (359 mg, 2.60 mmol) and N-methyl morpholine (263 mg, 2.6 mmol) in DMF (2.0 ml). After the mixture was stirred for 16 hours at room temperature, it was quenched with water and the solvents were allowed to evaporated under reduced pressure. The residue was purified through preparative HPLC (C-18 column, eluted with water/acetonitrile) to isolate desired product 5 (600 mg) as a white amorphous solid. $^1$HNMR (400 MHz, DMSO-d6, vs TMS) δ: 2.53(1H, dd, J=3.36, 3.34 Hz), 2.96(1H, dd, J=8.19, 8.30 Hz), 3.38(2H, dd, J=3.35, 3.36 Hz), 3.51(2H, dd, J=2.88, 2.88 Hz), 4.08(2H, s); 4.28(2H, m), 4.56(1H, dd, J=9.55, 9.56 Hz), 4.63(1H, m), 8.23(1H, m), 8.66(1H, d, J=2.30 Hz), 8.95(1H, d, J=1.66) ppm. Anal. Calcd for $C_{16}H_{20}N_6O_5 \cdot 2 H_2O \cdot 1.6TFA$, C, 38.77; H, 4.34; N, 14.13. Found: C, 38.78; H, 4.32; N, 14.06.

EXAMPLES 10, 11, 12, 13, 14, 15, 16, 17, 18 and 19 were prepared according to the following general synthetic scheme:

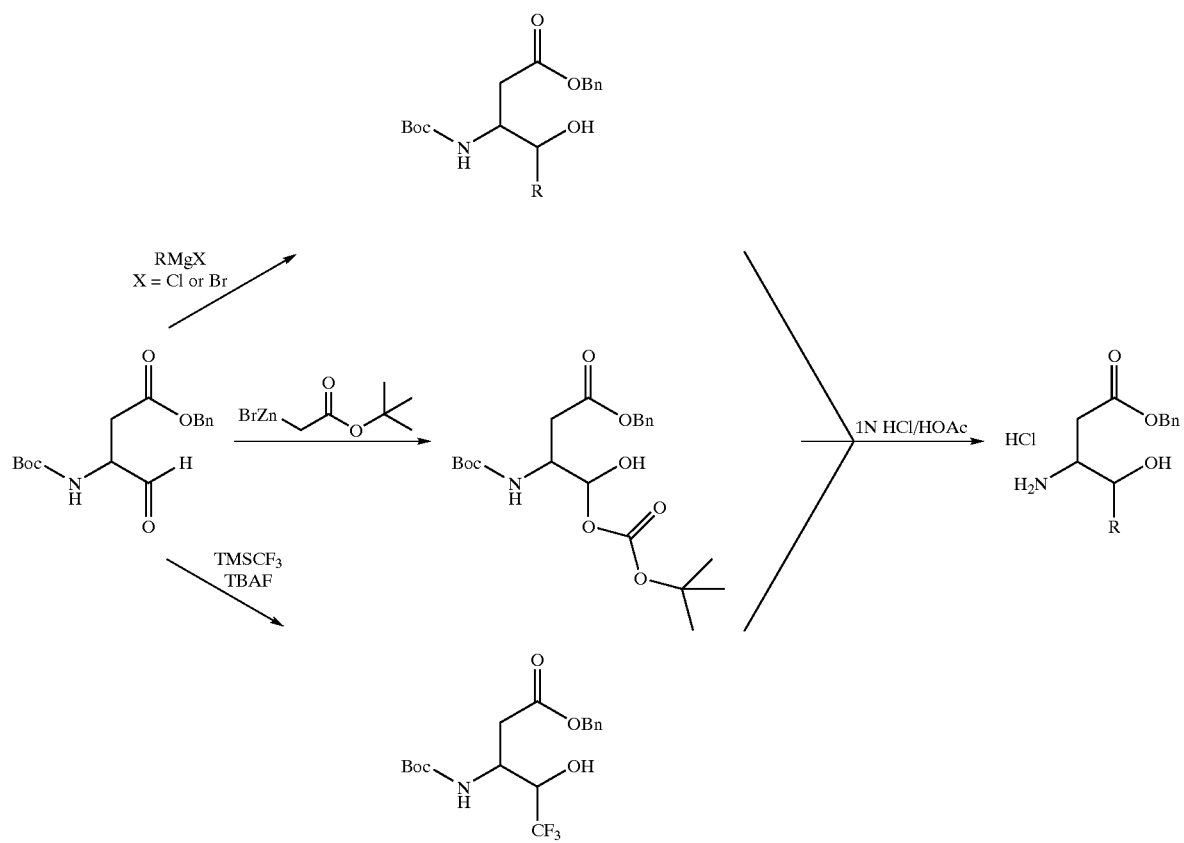

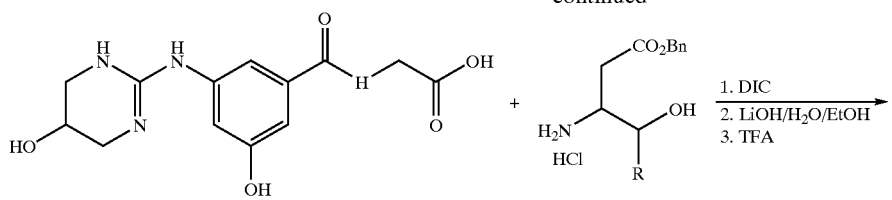

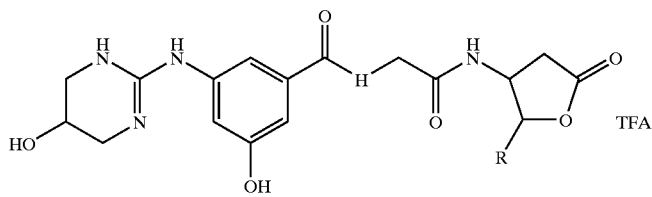

General procedures: Proton magnetic resonance spectra were recorded at 300 MHz and 400 MHz Varian spectrometers. High resolution Mass was performed by Analytical Lab of Searle. Commercial reagents were used upon receipt without further purification. Reaction were carried out under nitrogen unless otherwise noted. Compound 2i (R=p-fluorophenyl) was obtained from outside service company. Compound 1 (racemic) were provided by Carbogen.

General procedure for the preparation of 3-N-t-Boc-amino-4-hydroxyl-4-R-butyric acid benzyl ester:

Method A

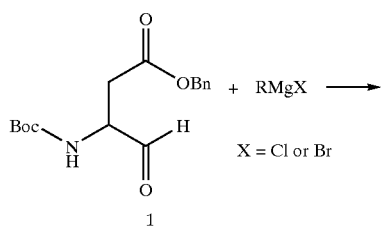

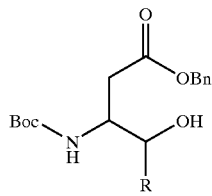

2b, R = allyl
2c, R = isopropyl
2f, R = pentyl
2g, R = decyl
2j, R = 3,5-dichlorophenyl Method A:

A solution of 5.2 g (16.94 mmol) aldehyde 1 in 130 mL anhydrous diethylether was cooled to −30° C. Solution turned cloudy while cooling. To this cold suspension was slowly added 16 mL 3.0M diethylether solution of methylmagnesium bromide along the side of the flask. The resulting mixture was stirred at −30° C. for 10 minutes then warmed up to 0° C. for one and a half hour then room temperature for 30 minutes. After that, the reaction was poured in to a separation funnel containing ice water. The aqueous phase was extracted with diethylether. The organic layer was washed successively with 1N aqueous HCl, saturated aqueous $NaHCO_3$ and brine. Then it was dried over sodium sulfate, filtered and concentrated to give a yellowish oil which was used directly in next step without purification.

Method B

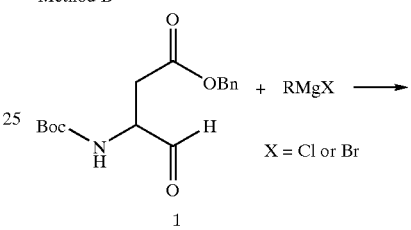

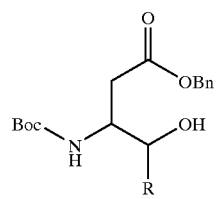

2d, R = isobutyl
2h, R = phenyl

Method B:

To a solution of 4.2 g (13.68 mmol) aldehyde 1 in 68.4 mL anhydrous THF at −50° C. was added 17.1 mL THF solution of i-butylmagnesium chloride (34.2 mmol) dropwise. The resulting solution was slowly warmed up to −20° C. over a period of two hours, then it was warmed up to 0° C. for one hour. After reaction, the mixture was poured on to ice water and was extracted with ethylacetate. The organic layer was washed successively with 1N aqueous HCl(×2), saturated aqueous $NaHCO_3$ and brine, then dried over $Na_2SO_4$, filtered and concentrated to give a yellowish oil.

Method C

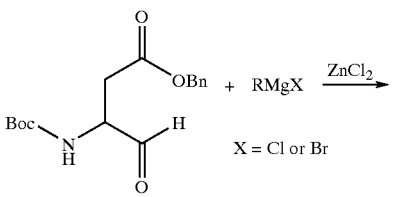

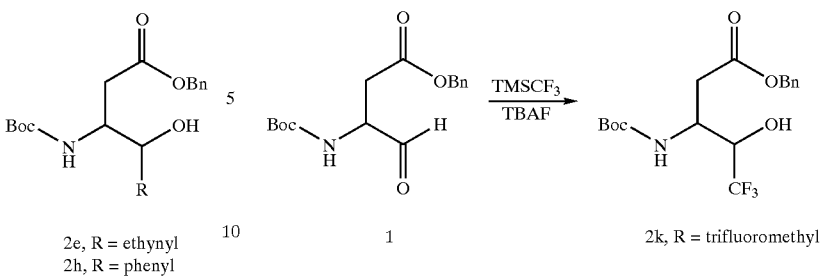

2e, R = ethynyl
2h, R = phenyl

1

2k, R = trifluoromethyl

Method C:

3.5 g (25.68 mmol) ZnCl$_2$ powder was dissolved in 30 mL THF and the solution was cooled to −10° C. Ethynylmagnesium bromide (51.79 mL, 0.5 M) in THF was slowly added along the side of the flask. The resulting mixture was stirred at −10° C. for an additional 10 minutes then warmed up to room temperature for 30 minutes before it was cooled to −40° C. The cold solution was then charged with aldehyde 1 (3.18 g, 10.358 mmol) in 15 mL THF and stirred at −40° C. for 30 minutes then warmed up to 0° C. for two hours. After stirring at room temperature for another one hour, the reaction was poured on to ice water and extracted with ethylacetate. The organic layer was washed successively with 1N aqueous HCl(×2), saturated aqueous NaHCO$_3$ and brine, then dried over Na$_2$SO$_4$, filtered and concentrated to give a yellowish oil. This crude oil was used directly in next step without further purification.

Preparation of Compound 2k:

A solution of 2.56 g (8.3 mmol) of aldehyde 1 in 20 mL THF was cooled to −40° C. To this cold solution was added 25 mL 0.5 M solution of Trimethyl(trifluoromethyl)silane (TMSCF$_3$) in THF followed by 0.5 mL THF solution of TBAF (0.5 mmol). The mixture was slowly warmed up to −10° C. over a period of two hours. Cooling bath was removed and the solution was allowed to warm up to room temperature for 30 minutes. After diluted with ethylacetate, the organic phase was washed with brine, dried over sodium sulfate, filtered and concentrated to give a brownish red oily residue which was used directly in next step.

Preparation of 3,5-dichloromagnesium bromide:

A three-necked round bottom flask equipped with condenser was flame dried and cooled to room temperature. Into this flask was placed 1.65 g magnesium turnings, 45 mL anhydrous diethylether and 10.05 g 1-bromo-3,5-dichlorobenzene. The mixture was cooled to 0° C. and one chip of iodine was added. The cooling bath was removed and the mixture was slowly warmed up to 50° C. using a water bath. When the bubbling stopped, another 5.1 g of 1-bromo-3,5-dichlorobenzene was added into this mixture followed by another chip of iodine. The mixture was heated to 60° C. and kept at 50° C. to 60° C. till all magnesium turnings has dissolved. The solution was then cooled to room temperature and used directly.

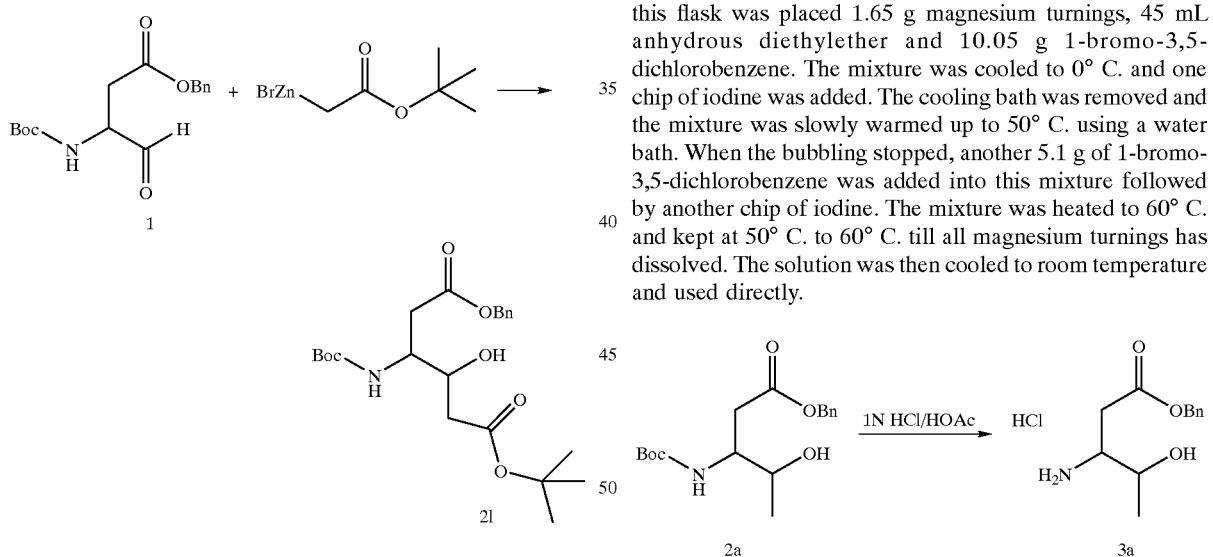

Preparation of Compound 2l:

To the cold suspension of 1.51 g (5.79 mmol) 2-t-butoxy-2-oxoethylzinc bromide in 29 mL THF at −40° C. was added 2.5 mL THF solution of 593 mg (1.93 mmol) aldehyde 1. The mixture was stirred at −40° C. for one hour then the cooling bath was replaced by ice water bath and the mixture was slowly warmed up to 5° C. over 18 hours. After warmed up to room temperature for one hour, the mixture was poured into a separation funnel containing 1N aqueous HCl. The aqueous layer was extracted with ethylacetate. The organic phase was washed successively with 1N aqueous HCl (×2), saturated aqueous NaHCO$_3$ and brine, then dried over Na$_2$SO$_4$, filtered and concentrated to give a yellowish oil which was used directly in next step.

General Procedure for the Preparation Compound 3a:

The crude mixture of 2a prepared from previous step was treated with 30 mL of 1N hydrogen chloride in acetic acid at room temperature. The progress of reaction was monitored by TLC. After about 30 minutes, reaction went to completion. Solvents were removed in vaco and the residue was co-evaporated with ethylacetate three times. The resulting brownish oil was partitioned between water and ethylacetate. The organic phase was disposed of. The aqueous layer was frozen dried to give a yellow solid which was used directly in next step without further purification.

Compound 3b–3l: compounds 3b–3l were prepared following the general procedure for the preparation of compound 3a respectively.

EXAMPLE 10

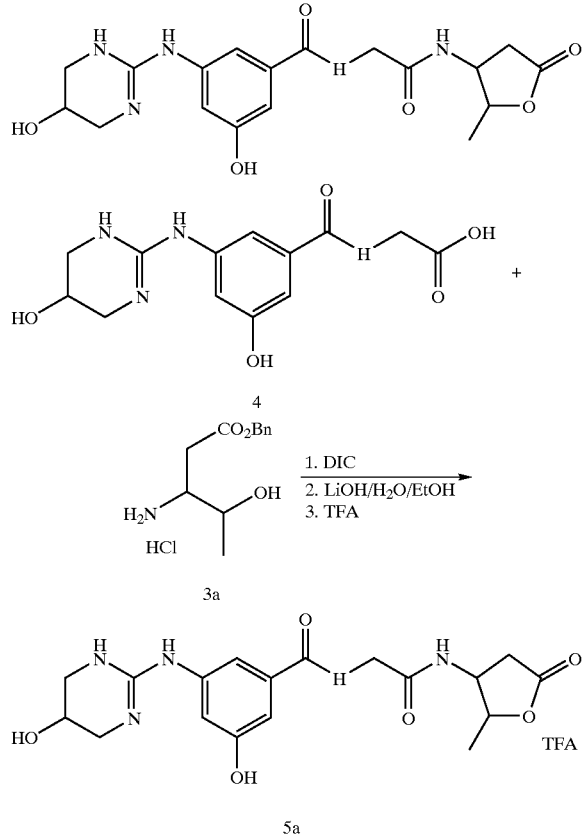

General Procedure for the Preparation of Compound 5a:

To a suspension of 4.85 g crude 3a and 4.6 g of compound 4 (prepared using similar procedure described in EXAMPLE 6, step 6a, 6b, 6c) in 15 mL DMA at room temperature was added 608 mg HOBT followed by 2.58 mL N,N-diisopropylcarbodiimide. The resulting mixture was stirred at room temperature overnight to give a brown solution. To this solution was added 4.7 g LiOH.H$_2$O and 5 mL of water. Ethanol was added into the mixture till a clear solution was obtained. The progress of reaction was monitored by Mass spectrometry and analytical HPLC. After about 40 minutes, saponification completed. The basic solution was acidified to pH=1 with trifluoroacetic acid and purified by reverse phase preparative HPLC. Those fractions having molecular weight of compound 5a were combined and frozen dried to give a white flake. The white flake was then treated with neat trifluoroacetic acid at room temperature. The mixture was purified again by reverse phase preparative HPLC to give compound 5a as a white flake. $^1$H NMR (400 MHZ, CD3OD): δ (ppm) 1.29 (d, J=6.4 Hz, 3H), 2.46 (dd, J=2.8, 18.0 Hz, 1H), 3.02 (dd, J=8.0, 18.0 Hz, 1H), 3.32(dd, J=3.2, 12.0 Hz, 2H), 3.44(dd, J=3.2, 12.0 Hz, 2H), 4.01 (t, J=4.4 Hz, 2H), 4.21–4.23 (m, 1H), 4.64–4.70 (m, 1H), 4.75–4.78 (m, 1H), 6.82 (dd, J=2.0, 2.0 Hz, 1H), 7.17 (dd, J=1.6, 1.6 Hz, 1H), 7.20 (dd, J=2.0, 2.0 Hz, 1H); MS (M+H): 432.2.

EXAMPLE 11

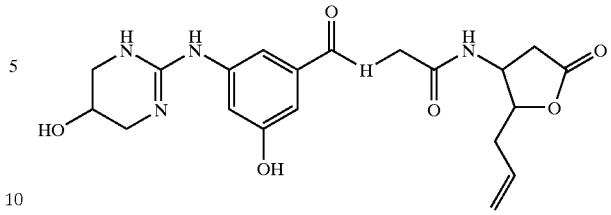

The title compound was prepared following the general procedure for the preparation of compound EXAMPLE 10. $^1$H NMR (300 MHZ, CD$_3$OD): δ (ppm) 2.46–2.57 (m, 2H), 2.57 (dd, J=5.7, 18.0 Hz, 1H), 2.99 (dd, J=8.4, 18.0 Hz, 1H), 3.34 (dd, J=3.3, 12.6 Hz, 2H), 3.49 (dd, J=3.0, 12.6 Hz, 2H), 4.02 (t, J=3.6 Hz, 2H), 4.24–4.28 (m, 1H), 4.38–4.49 (m, 2H), 5.11–5.27 (m, 2H), 5.80–5.94 (m, 1H), 6.87 (dd, J=2.1, 2.1 Hz, 1H), 7.21 (dd, J=2.1, 2.1 Hz, 1H), 7.24 (dd, J=2.1, 2.1 Hz, 1H); Theoretical MS (M+H): 406.1727; Found: 406.1716.

EXAMPLE 11

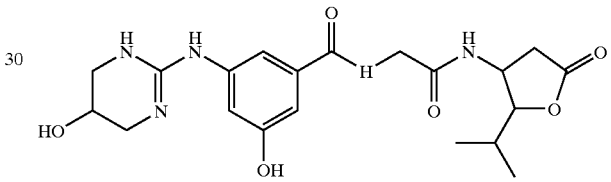

The title compound was prepared following the general procedure for the preparation of compound EXAMPLE 10. $^1$H NMR (400 MHZ, CD$_3$OD): δ (ppm) 0.87 (d, J=6.4 Hz, 3H), 1.09 (d, J=6.8 Hz, 3H), 1.94–1.99 (m, 1H), 2.41 (d, J=18.0, 1H), 3.05 (dd, J=7.2, 18.0 Hz, 1H), 3.30 (dd, J=3.6, 12.4 Hz, 2H), 3.44 (dd, J=2.4, 12.4 Hz, 2H), 3.98 (t, J=4.4 Hz, 2H), 4.13–4.17 (m, 1H), 4.21–4.23 (m, 1H), 4.74–4.80 (m, 1H), 6.82 (dd, J=2.0, 2.0 Hz, 1H), 7.16 (dd, J=2.0, 2.0 Hz, 1H), 7.19 (dd, J=2.0, 2.0 Hz, 1H); Theoretical MS (M+H): 434.2040; Found: 434.2023.

EXAMPLE 12

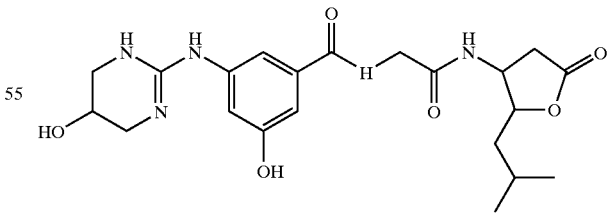

The title compound was prepared following the general procedure for the preparation of compound EXAMPLE 10. $^1$H NMR (400 MHZ, CD$_3$OD): δ (ppm) 0.94–0.97 (m, 6H), 1.37–1.43 (m, 1H), 1.59–1.66 (m, 1H), 1.73–1.78 (m, 1H), 2.42 (dd, J=1.6, 17.6 Hz, 1H), 3.03 (dd, J=7.6, 17.6 Hz, 1H), 3.30 (dd, J=3.6, 12.4 Hz, 2H), 3.44 (dd, J=2.4, 12.4 Hz, 2H), 3.99 (brs, 1H), 4.21–4.23 (m, 1H), 4.69–4.72 (m, 2H), 6.83 (dd, J=2.4, 2.4 Hz, 1H), 7.17 (dd, J=1.6, 1.6 Hz, 1H), 7.20 (dd, J=1.6, 1.6 Hz, 1H); Theoretical MS (M+H): 448.2196; Found: 448.2205.

EXAMPLE 13

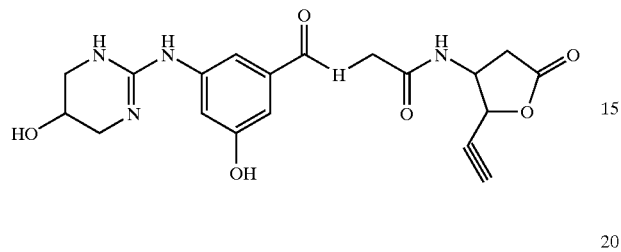

The title compound was prepared following the general procedure for the preparation of compound EXAMPLE 10. $^1$H NMR (400 MHZ, CD$_3$OD): δ (ppm) 2.58 (dd, J=6.0, 17.6 Hz, 1H), 2.93 (dd, J=8.0, 17.6 Hz, 1H), 3.22 (2s, 1H), 3.31 (dd, J=3.6, 12.4 Hz, 2H), 3.44 (dd, J=2.8, 12.4 Hz, 2H), 4.02 (d, J=17.2, 1H), 4.09 (d, J=17.2 Hz, 1H), 4.21–4.23 (m, 1H), 4.80–4.90 (obscure m, 1H), 5.39 & 5.41 (2d, J=2.4 Hz, 1H), 6.83 (dd, J=2.4, 2.4 Hz, 1H), 7.17 (dd, J=1.6, 1.6 Hz, 1H), 7.19 (dd, J=1.6, 1.6 Hz, 1H); Theoretical MS (M+H): 416.1570; Found: 416.1579.

EXAMPLE 14

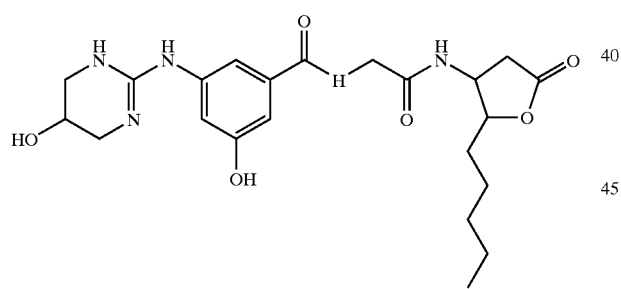

The title compound was prepared following the general procedure for the preparation of compound EXAMPLE 10, except no saponification was carried out. After coupling with compound 4, the mixture was treated with trifluoroacetic acid and water. When lactonization has completed, the resulting mixture was purified by reverse phase preparative HPLC. $^1$H NMR (400 MHZ, CD$_3$OD): δ (ppm) 0.89 (t, J=7.2 Hz, 3H), 1.28–1.36 (m, 6H), 1.54–1.74 (m, 2H), 2.43 (dd, J=2.4, 18.0 Hz, 1H), 3.02 (dd, J=8.0, 18.0 Hz, 1H), 3.30 (dd, J=3.6, 12.4 Hz, 2H), 3.44 (dd, J=2.8, 12.4 Hz, 2H), 3.99 (brs, 2H), 4.21–4.23 (m, 1H), 4.56–4.61 (m, 1H), 4.69–4.74 (m, 1H), 6.83 (t, J=2.0 Hz, 1H), 7.17 (t, J=1.6 Hz, 1H), 7.20 (t, J=1.6 Hz, 1H); Theoretical MS (M+H): 462.2353; Found: 462.2352.

EXAMPLE 15

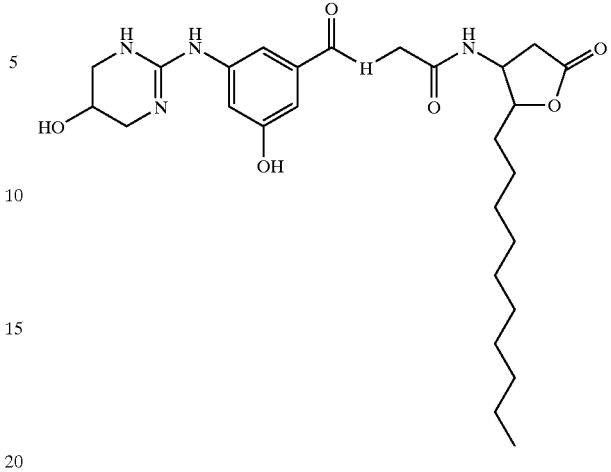

The title compound was prepared following the general procedure for the preparation of compound EXAMPLE 10. $^1$H NMR (400 MHZ, CD$_3$OD): δ (ppm) 0.88 (t, J=6.8 Hz, 3H), 1.27–1.70 (m, 18H), 2.43 (dd, J=2.0, 17.6 Hz, 1H), 3.02 (dd, J=8.0, 17.6 Hz, 1H), 3.30 (dd, J=3.6, 12.4 Hz, 2H), 3.44 (dd, J=2.8, 12.4 Hz, 2H), 3.99 (dd, J=6.8, 6.8 Hz, 2H), 4.21–4.23 (m, 1 H), 4.54–4.62 (m, 1H), 4.68–4.74 (m, 1H), 6.82 (t, J=2.0 Hz, 1H), 7.16 (t, J=1.6 Hz, 1H), 7.19 (t, J=1.6 Hz, 1H); Theoretical MS (M+H): 532.3135; Found: 532.3146.

EXAMPLE 16

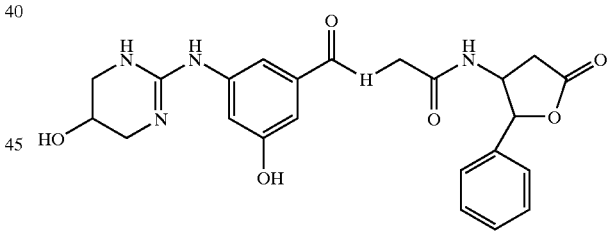

The title compound was prepared following the general procedure for the preparation of compound EXAMPLE 10, except no saponification was carried out. After coupling with compound 4, the mixture was treated with trifluoroacetic acid and water. When lactonization has completed, the resulting mixture was purified by reverse phase preparative HPLC. $^1$H NMR (400 MHZ, CD$_3$OD): δ (ppm) 2.64 (dd, J=5.2, 18.0 Hz, 1H), 2.99 (dd, J=8.4, 18.0 Hz, 1H), 3.30 (dd, J=3.6, 12.4 Hz, 2H), 3.44 (dd, J=2.4, 12.4 Hz, 2H), 3.99 (d, J=16.4 Hz, 1H), 4.04 (d, J=16.4 Hz, 1H), 4.21–4.24 (m, 1H), 4.50–4.55 (m, 1H), 5.44 (d, J=4.4, 1H), 6.83 (t, J=2.4 Hz, 1H), 7.17 (t, J=2.0 Hz, 1H), 7.21 (t, J=2.4 Hz, 1H), 7.25–7.43 (m, 5H); Theoretical MS (M+H): 468.1883; Found: 468.1880.

EXAMPLE 17

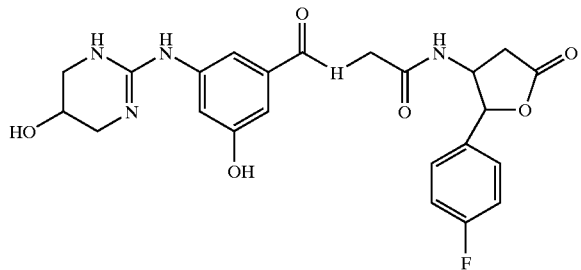

The title compound was prepared following the general procedure for the preparation of compound EXAMPLE 10. $^1$H NMR (400 MHZ, $CD_3OD$): δ (ppm) 2.61 (dd, J=2.8, 17.6 Hz, 1H), 3.17 (dd, J=8.4, 17.6 Hz, 1H), 3.30 (dd, J=3.6, 12.8 Hz, 2H), 3.44 (dd, J=2.8, 12.8 Hz, 2H), 3.52 (d, J=16.4 Hz, 1H), 3.76 (d, J=16.4 Hz, 1H), 4.21–4.23 (m, 1H), 4.94–4.97 (m, 1H), 5.75 (d, J=5.6 Hz, 1H), 6.81 (t, J=2.4 Hz, 1H), 7.05–7.13 (m, 4H), 7.28–7.32 (m, 2H); Theoretical MS (M+H): 486.1789; Found: 486.1801.

EXAMPLE 18

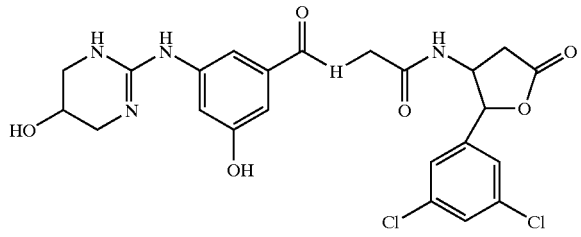

The title compound was prepared following the general procedure for the preparation of compound EXAMPLE 10. Diastereomer a: $^1$H NMR (400 MHZ, $CD_3OD$): δ (ppm) 2.61 (dd, J=2.0, 18.0 Hz, 1H), 3.19.(dd, J=8.0, 18.0 Hz, 1H), 3.30 (dd, J=3.6, 12.4 Hz, 2H), 3.44 (dd, J=2.4, 12.4 Hz, 2H), 3.53 (d, J=16.4 Hz, 1H), 3.78 (d, J=16.4 Hz, 1H), 4.21–4.23 (m, 1H), 4.96–5.02 (m, 1H), 5.73 (d, J=5.6 Hz, 1H), 6.80 (t, J=2.0 Hz, 1H), 7.09 (t, J=2.0 Hz, 1H), 7.13 (t, J=2.0 Hz, 1H), 7.27–7.28 (m, 2H), 7.37 (t, J=2.0 Hz, 1H). Diastereomer b): $^1$H NMR (400 MHZ, $CD_3OD$): δ (ppm) 2.65 (dd, J=5.6, 18.0 Hz, 1H), 3.0 (dd, J=8.4, 18.0 Hz, 1H), 3.30 (dd, J=3.6, 12.4 Hz, 2H), 3.44 (dd, J=2.4, 12.4 Hz, 2H), 4.01 (brs, 2H), 4.21–4.23 (m, 1H), 4.48–4.53 (m, 1H), 5.40 (d, J=4.8 Hz, 1H), 6.83 (t, J=2.0 Hz, 1H), 7.19 (t, J=2.0 Hz, 1H), 7.22 (t, J=2.0 Hz, 1H), 7.43 (brs, 3H).

EXAMPLE 19

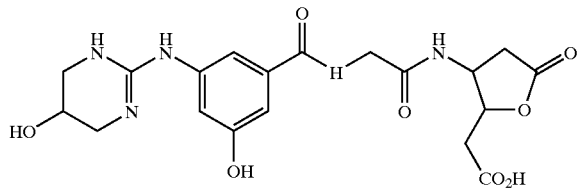

The title compound was prepared following the general procedure for the preparation of compound EXAMPLE 10, except no saponification was carried out. After coupling with compound 4, the mixture was treated with trifluoroacetic acid and water. When lactonization has completed, the resulting mixture was purified by reverse phase preparative HPLC. $^1$H NMR (400 MHZ, $CD_3OD$): δ (ppm) 2.58 (dd, J=6.0, 18.0 Hz, 1H), 2.73 (dd, J=7.6, 16.8 Hz, 1H), 2.88 (dd, J=4.4, 16.8 Hz, 1H), 3.01 (dd, J=8.8, 18.0 Hz, 1H), 3.31 (dd, J=3.6, 12.4 Hz, 2H), 3.44 (dd, J=2.4, 12.4 Hz, 2H), 4.00 (brs, 2H), 4.20–4.24 (m, 1H), 4.45–4.50 (m, 1H), 4.65–4.70 (m, 1H), 6.83 (t, J=2.0 Hz, 1H), 7.17 (t, J=2.0 Hz, 1H), 7.2 (t, J=2.0 Hz, 1H).

Activity of the compounds of the present invention can be tested in the following assays. Compounds of the present invention antagonize the $\alpha_v\beta_3$ integrin with an $IC_{50}$ of 0.1 nM to 100 μM in the 293-cell assay. Similarly these compounds also antagonized the $\alpha_v\beta_5$ integrin with an $IC_{50}$ of <50 μM in the cell adhesion assay.

Vitronectin Adhesion Assay

Human vitronectin receptors $\alpha_v\beta_3$ and $\alpha_v\beta_5$ are purified from human placenta as previously described [Pytela et al., *Methods in Enzymology*, 144:475–489 (1987)]. Human vitronectin is purified from fresh frozen plasma as previously described [Yatohgo et al., *Cell Structure and Function*, 13:281–292 (1988)]. Biotinylated human vitronectin is prepared by coupling NHS-biotin from Pierce Chemical Company (Rockford, Ill.) to purified vitronectin as previously described [Charo et al. *J. Biol. Chem.*, 266(3):1415–1421 (1991)]. Assay buffer, OPD substrate tablets, and RIA grade BSA are obtained from Sigma (St. Louis, Mo.). Anti-biotin antibody is obtained from Sigma (St. Luois, Mo.). Nalge Nunc-Immuno microtiter plates were obtained from Nalge Company (Rochester, N.Y.).

This assay is essentially the same as previously reported [Niiya et al., *Blood*, 70:475–483 (1987)]. The purified human vitronectin receptors $\alpha_v\beta_3$ and $\alpha_v\beta_5$ are diluted from stock solutions to 1.0 μg/mL in Tris-buffered saline containing 1.0 mM $Ca^{++}$, $Mg^{++}$, and $Mn^{++}$, pH 7.4 ($TBS^{+++}$). The diluted receptors are immediately transferred to Nalge Nunc-Immuno microtiter plates at 100 μL/well (100 ng receptor/well). The plates are sealed and incubated overnight at 4° C. to allow the receptors to bind to the wells. All remaining steps are at room temperature. The assay plates are emptied and 200 μL of 1% RIA grade BSA in $TBS^{+++}$ ($TBS^{+++}$/BSA) are added to block exposed plastic surfaces. Following a 2 hour incubation, the assay plates are washed with $TBS^{+++}$ using a 96 well plate washer. Logarithmic serial dilution of the test compound and controls are made starting at a stock concentration of 2 mM and using 2 nM biotinylated vitronectin in $TBS^{+++}$/BSA as the diluent. This premixing of labeled ligand with test (or control) ligand, and subsequent transfer of 50 μL aliquots to the assay plate is carried out with a CETUS Propette robot; the final concentration of the labeled ligand is 1 nM and the highest concentration of test compound is $1.0\times10^{-4}$ M. The competition occurred for two hours after which all wells are washed with a plate washer as before. Affinity purified horseradish peroxidase labeled goat anti-biotin antibody is diluted 1:2000 in $TBS^{+++}$/BSA and 125 μL is added to each well. After 45 minutes, the plates are washed and incubated with $OPD/H_2O_2$ substrate in 100 mM/L Citrate buffer, pH 5.0. The plate is read with a microtiter plate reader at a wavelength of 450 nm and when the maximum-binding control wells reached an absorbance of about 1.0, the final $A_{450}$ are recorded for analysis. The data are analyzed using a macro written for use with the EXCEL spreadsheet program. The mean, standard deviation, and % CV were determined for duplicate concentrations. The mean $A_{450}$ values are normalized to the mean of four maximum-binding controls (no competitor added)(B-MAX). The normalized values are subjected to a four parameter curve fit algorithm [Rodbard et al., *Int. Atomic Energy Agency, Vienna*, pp 469 (1977)], plotted on a semi-log scale, and the computed concentration corresponding to inhibition of 50% of the maximum binding of biotinylated vitronectin ($IC_{50}$) and corresponding $R^2$ is reported for those compounds exhibiting greater than 50% inhibition at the highest concentration tested; otherwise the $IC_{50}$ is reported as being greater than the highest concentration tested.

Purified IIb/IIIa Receptor Assay

Human fibrinogen receptor ($\alpha_v\beta_3$) is purified from outdated platelets. (Pytela, R., Pierschbacher, M. D., Argraves, S., Suzuki, S., and Rouslahti, E. "Arginine-Glycine-Aspartic acid adhesion receptors", *Methods in Enzymology* 144 (1987):475–489.) Human vitronectin is purified from fresh frozen plasma as described in Yatohgo, T., Izumi, M., Kashiwagi, H., and Hayashi, M., "Novel purification of vitronectin from human plasma by heparin affinity chromatography," *Cell Structure and Function* 13(1988): 281–292. Biotinylated human vitronectin is prepared by coupling NHS-biotin from Pierce Chemical Company (Rockford, Ill.) to purified vitronectin as previously described. (Charo, I. F., Nannizzi, L., Phillips, D. R., Hsu, M. A., Scarborough, R. M., "Inhibition of fibrinogen binding to GP IIb/IIIa by a GP IIIa peptide", *J. Biol. Chem.* 266(3) (1991): 1415–1421.) Assay buffer, OPD substrate tablets, and RIA grade BSA are obtained from Sigma (St. Louis, Mo.). Anti-biotin antibody is obtained from Sigma (St. Louis, Mo.). Nalge Nunc-Immuno microtiter plates are obtained from (Rochester, N.Y.). ADP reagent is obtained from Sigma (St. Louis, Mo.).

This assay is essentially the same reported in Niiya, K., Hodson, E., Bader, R., Byers-Ward, V. Koziol, J. A., Plow, E. F. and Ruggeri, Z. M., "Increased surface expression of the membrane glycoprotein IIb/IIIa complex induced by platelet activation: Relationships to the binding of fibrinogen and platelet aggregation", *Blood* 70(1987):475–483. The purified human fibrinogen receptor ($\alpha_v\beta_3$) is diluted from stock solutions to 1.0 μg/mL in Tris-buffered saline containing 1.0 mM $Ca^{++}$, $Mg^{++}$, and $Mn^{++}$, pH 7.4 (TBS). The diluted receptor is immediately transferred to Nalge Nunc-Immuno microtiter plates at 100 μL/well (100 ng receptor/well). The plates are sealed and incubated overnight at 4° C. to allow the receptors to bind to the wells. All remaining steps are at room temperature. The assay plates are emptied and 200 μL of 1% RIA grade BSA in $TBS^{+++}$ ($TBS^{+++}$/BSA) are added to block exposed plastic surfaces. Following a 2 hour incubation, the assay plates are washed with $TBS^{+++}$ using a 96 well plate washer. Logarithmic serial dilution of the test compound and controls are made starting at a stock concentration of 2 mM and using 2 nM biotinylated vitronectin in $TBS^{+++}$/BSA as the diluent. This premixing of labeled ligand with test (or control) ligand, and subsequent transfer of 50 μL aliquots to the assay plate is carried out with a CETUS Propette robot; the final concentration of the labeled ligand is 1 nM and the highest concentration of test compound is $1.0 \times 10^{-4}$ M. The competition occurred for two hours after which all wells are washed with a plate washer as before. Affinity purified horseradish peroxidase labeled goat anti-biotin antibody is diluted 1:2000 in $TBS^{+++}$/BSA and 125 μL are added to each well. After 45 minutes, theplates are washed and incubated with $ODD/H_2O_2$ substrate in 100 mM/L citrate buffer, pH 5.0. The plate was read with a microtiter plate reader at a wavelength of 450 nm and when the maximum-binding control wells reached an absorbance of about 1.0, the final $A_{450}$ are recorded for analysis. The data are analyzed using a macro written for use with the EXCELJ spreadsheet program. The mean, standard deviation, and % CV are determined for duplicate concentrations. The mean $A_{450}$ values are normalized to the mean of four maximum-binding controls (no competitor added)(B-MAX). The normalized values are subjected to a four parameter curve fit algorithm, [Robard et al., *Int. Atomic Energy Agency, Vienna*, pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino]-1-oxopentyl]amino]-1-oxoethyl]amino]-3-pyridinepropanoic acid [U.S. Pat. No. 5,602,155 Example 1] which is a potent $\alpha_v\beta_3$ antagonist ($IC_{50}$ in the range 3–10 nM) is included on each plate as a positive control.

Human Platelet Rich Plasma Assays

Healthy aspirin free donors are selected from a pool of volunteers. The harvesting of platelet rich plasma and subsequent ADP induced platelet aggregation assays are performed as described in Zucker, M. B., "Platelet Aggregation Measured by the Photometric Method", *Methods in Enzymology* 169(1989):117–133. Standard venipuncture techniques using a butterfly allowed the withdrawal of 45 mL of whole blood into a 60 mL syringe containing 5 mL of 3.8% trisodium citrate. Following thorough mixing in the syringe, the anti-coagulated whole blood is transferred to a 50 mL conical polyethylene tube. The blood is centrifuged at room temperature for 12 minutes at 200×g to sediment non-platelet cells. Platelet rich plasma is removed to a polyethylene tube and stored at room temperature until used. Platelet poor plasma is obtained from a second centrifugation of the remaining blood at 2000×g for 15 minutes. Platelet counts are typically 300,000 to 500,000 per microliter. Platelet rich plasma (0.45 mL) is aliquoted into siliconized cuvettes and stirred (1100 rpm) at 37° C. for 1 minute prior to adding 50 uL of pre-diluted test compound. After 1 minute of mixing, aggregation is initiated by the addition of 50 uL of 200 uM ADP. Aggregation is recorded for 3 minutes in a Payton dual channel aggregometer (Payton Scientific, Buffalo, N.Y.). The percent inhibition of maximal response (saline control) for a series of test compound dilutions is used to determine a dose response curve. All compounds are tested in duplicate and the concentration of half-maximal inhibition ($IC_{50}$) is calculated graphically from the dose response curve for those compounds which exhibited 50% or greater inhibition at the highest concentration tested; otherwise, the $IC_{50}$ is reported as being greater than the highest concentration tested.

Cell Assays for Potency and Selectivity

While the $\beta_3$ subunit of $\alpha_v\beta_3$ is only known to complex with $\alpha_v$ or $\alpha_{IIb}$, the $\alpha_v$ subunit complexes with multiple β subunits. The three $\alpha_v$ integrins most homologous with $\alpha_v\beta_3$ are $\alpha_v\beta_1$, $\alpha_v\beta_5$ and $\alpha_v\beta_6$, with 43%, 56% and 47% amino acid identity in the β subunits, respectively. To evaluate the selectivity of compounds between the integrins $\alpha_v\beta_3$ and $\alpha_v\beta_6$, cell-based assays were established using the 293 human embryonic kidney cell line. 293 cells express $\alpha_v\beta_1$, but little to no detectable $\alpha_v\beta_3$ or $\alpha_v\beta_6$. cDNAs for $\beta_3$ and $\beta_6$ were transfected separately into 293 cells to generate 293-β3 and 293-β6 cells, respectively. High surface expression of $\alpha_v\beta_3$ and $\alpha_v\beta_6$ was confirmed by flow cytometry. Conditions were established for each cell line in which cell adhesion to immobilized human vitronectin was mediated by the appropriate integrin, as determined by a panel of integrin-specific, neutralizing monoclonal antibodies. Briefly, cells were incubated with inhibitor in the presence of 200 uM $Mn^{2+}$, allowed to adhere to immobilized vitronectin, washed, and adherent cells are detected endoenous alkaline phosphatase and para-nitrophenyl phosphate. An 8-point dose-response curve using either 10-fold or 3-fold dilutions of compound was evaluated by fitting a four-parameter logistic, nonlinear model (using SAS).

To evaluate compound potency for membrane-bound $\alpha_v\beta_6$ an additional cell-based adhesion assay was established using the HT-29 human colon carcinoma cell line. High surface expression of $\alpha_v\beta_6$ on HT-29 cells was confirmed by flow cytometry. Conditions were established in which cell adhesion to immobilized human latency associated peptide (LAP) was mediated by the $\alpha_v\beta_6$ as determined by a panel of integrin-specific, neutralizing monoclonal antibodies. Briefly, cells were incubated with inhibitor in the presence of 200 uM $Mn^{2+}$, allowed to adhere to immobilized LAP, washed, and adherent cells are detected by quantifying endogenous alkaline phosphatase using para-nitrophenyl phosphate. An 8-point dose-response curve using either 10-fold or 3-fold dilutions of compound was evaluated by fitting a four-parameter logistic, nonlinear model (using SAS). The compounds evaluated were relatively ineffective at inhibition of $\alpha_v\beta_6$-mediated cell adhesion. The selective antagonism of the $\alpha_v\beta_3$ integrin is viewed as desirable in this class of compounds, as $\alpha_v\beta_6$ may also play a role in normal physiological processes of tissue repair and cellular turnover that routinely occur in the skin and pulmonary tissues.

What is claimed is:

1. A compound, isomer of the compound, enantiomer of the compound, tautomer of the compound, racemate of the compound, or polymorph of the compound, wherein:

the compound corresponds in structure to Formula I:

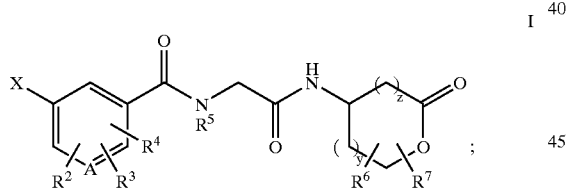

X is selected from the group consisting of:

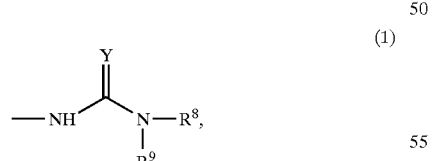

(1)

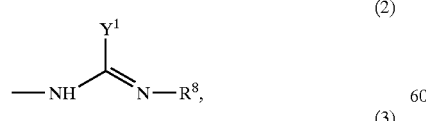

(2)

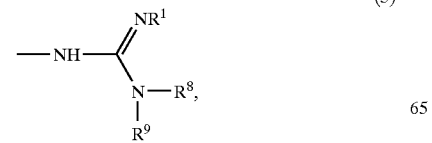

(3)

-continued
and

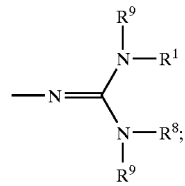

(4)

Y is selected from the group consisting of $N-R^1$, O, and S;

y and z are independently selected from the group consisting of 0, 1, 2, and 3;

A is N or C;

as to $R^1$:

X corresponds in structure to Formula (1), and $R^1$ is selected from the group consisting of H, alkyl, phenyl, hydroxy, alkoxy, cyano, nitro, amino, alkenyl, alkynyl, amido, alkylcarbonyl, phenylcarbonyl, alkoxycarbonyl, phenyloxycarbonyl, haloalkylcarbonyl, haloalkoxycarbonyl, alkylthiocarbonyl, phenylthiocarbonyl, acyloxymethoxycarbonyl, alkyl substituted with one or more substituents selected from the group consisting of lower alkyl, halogen, hydroxyl, haloalkyl, cyano, nitro, carboxyl, amino, alkoxy, phenyl, and phenyl substituted with one or more substituents selected from the group consisting of halogen, haloalkyl, lower alkyl, alkoxy, cyano, alkylsulfonyl, alkylthio, nitro, carboxyl, amino, hydroxyl, sulfonic acid, sulfonamide, phenyl, naphthyl, monocyclic heterocycles, and fused monocyclic heterocycles, phenyl substituted with one or more substituents selected from the group consisting of halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, phenyl, naphthyl, monocyclic heterocycles, and fused monocyclic heterocycles, monocyclic heterocycles, and monocyclic heterocycles substituted with one or more substituents selected from the group consisting of halogen, haloalkyl, lower alkyl, alkoxy, amino, nitro, hydroxy, carboxyl derivatives, cyano, alkylthio, alkylsulfonyl, sulfonic acid, sulfonamide, phenyl and naphthyl; or X corresponds in structure to Formula (1), and $R^1$ and $R^8$, together with the atoms to which they are bonded, form a 4–12 membered dinitrogen-containing heterocycle optionally substituted with one or more substituents selected from the group consisting of lower alkyl, hydroxy, alkoxy, halo, phenyl, amino, carboxyl, carboxyl ester, and fused phenyl; or X corresponds in structure to Formula (1), and $R^1$ and $R^8$, together with the atoms to which they are bonded, form a 5 membered heteroaromatic ring optionally substituted with one or more substituents selected from the group consisting of lower alkyl, phenyl, and hydroxy; or X corresponds in structure to Formula (1), and $R^1$ and $R^8$, together with the atoms to which they are bonded, form a 5 membered heteroaromatic ring fused with a phenyl group; or X corresponds in structure to Formula (3), and $R^1$ and $R^8$, together with the atoms to which they are bonded, form a 5–8 membered dinitrogen-containing heterocycle optionally substituted with one or more substituents selected from the group consisting of lower alkyl, hydroxy, phenyl, or carboxyl derivatives; or X corresponds in structure to Formula (4), and $R^1$ and $R^8$, together with the atoms to which they are bonded, form a 5–8 membered dinitrogen-containing heterocycle optionally substituted with hydroxy, phenyl, or alkyl;

as to $R^8$:

X corresponds in structure to Formula (1) or (2), and $R^8$ is selected from the group consisting of H, alkyl, alkenyl, alkynyl, phenylalkyl, amino, alkylamino, hydroxy, alkoxy, phenylamino, amido, alkylcarbonyl, phenylcarbonyl, alkoxycarbonyl, phenyloxy, phenyloxycarbonyl, haloalkylcarbonyl, haloalkoxycarbonyl, alkylthiocarbonyl, phenylthiocarbonyl, acyloxymethoxycarbonyl, cycloalkyl, bicycloalkyl, phenyl, acyl, benzoyl, alkyl substituted with one or more substituents selected from the group consisting of lower alkyl, halogen, hydroxy, haloalkyl, cyano, nitro, carboxyl derivatives, amino, alkoxy, thio, alkylthio, sulfonyl, phenyl, phenylalkyl, phenyl substituted with one or more substituents selected from the group consisting of halogen, haloalkyl, lower alkyl, alkoxy, methylenedioxy, ethylenedioxy, alkylthio, haloalkylthio, thio, hydroxy, cyano, nitro, carboxyl derivatives, phenyloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, phenyl, naphthyl, monocyclic heterocycles, fused monocyclic heterocycles, phenyl substituted with one or more substituents selected from the group consisting of halogen, haloalkyl, lower alkyl, alkoxy, methylenedioxy, ethylenedioxy, alkylthio, haloalkylthio, thio, hydroxy, cyano, nitro, carboxyl derivatives, phenyloxy, amido, acylamino, amino, alkylamino, dialkylamino, trifluoroalkoxy, trifluoromethylsulfonyl, alkylsulfonyl, sulfonic acid, sulfonamide, phenyl, naphthyl, monocyclic heterocycles, and fused monocyclic heterocycles, monocyclic heterocycles, monocyclic heterocycles substituted with one or more substituents selected from the group consisting of halogen, haloalkyl, lower alkyl, alkoxy, phenyloxy, amino, nitro, hydroxy, carboxyl derivatives, cyano, alkylthio, alkylsulfonyl, phenyl, naphthyl, monocyclic and bicyclic heterocyclicalkyls, and $—SO_2R^{10}$; or X corresponds in structure to Formula (1) or (2), and $R^8$ is

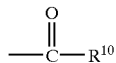

or

X corresponds in structure to Formula (1), and $R^8$ and $R^9$, together with the nitrogen to which they are bonded, form a 4–12 membered mononitrogen-containing monocyclic or bicyclic ring, wherein the ring:
is optionally substituted with one or more substituents selected from the group consisting of lower alkyl, carboxyl derivatives, phenyl, and hydroxy, and may contain an additional heteroatom selected from the group consisting of O, N, and S; or X corresponds in structure to Formula (1), and $R^8$ and $R^1$, together with the atoms to which they are bonded, form a 4–12 membered dinitrogen-containing heterocycle optionally substituted with one or more substituents selected from the group consisting of lower alkyl, hydroxy, alkoxy, halo, phenyl, amino, carboxyl, carboxyl ester, and fused phenyl; or X corresponds in structure to Formula (1), and $R^8$ and $R^1$, together with the atoms to which they are bonded, form a 5 membered heteroaromatic ring optionally substituted with one or more substituents selected from the group consisting of lower alkyl, phenyl, and hydroxy; or X corresponds in structure to Formula (1), and $R^8$ and $R^1$, together with the atoms to which they are bonded, form a 5 membered heteroaromatic ring fused with a phenyl group; or X corresponds in structure to Formula (2), and $R^8$ and $R^{11}$, together with the atoms to which they are bonded, form a 4–12 membered mononitrogen- and monosulfur- or monooxygen-containing heterocyclic ring optionaily substituted with lower alkyl, hydroxy, phenyl, carboxyl, carboxyl ester, or fused phenyl; or X corresponds in structure to Formula (2), and $R^8$ and $R^{11}$, together with the atoms to which they are bonded, form thiazole, oxazole, benzoxazole, or benzothiazole; or X corresponds in structure to Formula (2), $Y^1$ is carbon such that $R^8$ and $Y^1$, together with the atoms to which they are bonded, form a 4–12 membered mononitrogen- or dinitrogen-containing ring optionally substituted with alkyl, phenyl, or hydroxy; or X corresoonds in structure to Formula (3), and $R^8$ and $R^1$, together with the atoms to which they are bonded, form a 5–8 membered dinitrogen-containing heterocycle optionally substituted with one or more substituents selected from the group consisting of lower alkyl, hydroxy, phenyl, or carboxyl derivatives;

X corresponds in structure to Formula (4) and $R^8$ and $R^1$, together with the atoms to which they are bonded, form a 5–8 membered dinitrogen-containing heterocycle optionally substituted with hydroxy, phenyl, or alkyl;

as to $R^9$:

X corresponds in structure to Formula (1), and $R^9$ is selected from the group consisting of H, alkyl, alkenyl, alkynyl, phenylalkyl, amino, alkylamino, hydroxy, alkoxy, phenylamino, amido, alkylcarbonyl, phenylcarbonyl, alkoxycarbonyl, phenyloxy, phenyloxycarbonyl, haloalkylcarbonyl, haloalkoxycarbonyl, alkylthiocarbonyl, phenylthiocarbonyl, acyloxymethoxycarbonyl, cycloalkyl, bicycloalkyl, phenyl, acyl, benzoyl, alkyl substituted with one or more substituents selected from the group consisting of lower alkyl, halogen, hydroxy, haloalkyl, cyano, nitro, carboxyl derivatives, amino, alkoxy, thio, alkylthio, sulfonyl, phenyl, phenylalkyl, phenyl substituted with one or more substituents selected from the group consisting of halogen, haloalkyl, lower alkyl, alkoxy, methylenedioxy, ethylenedioxy, alkylthio, haloalkylthio, thio, hydroxy, cyano, nitro, carboxyl derivatives, phenyloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, phenyl, naphthyl, monocyclic heterocycles, fused monocyclic heterocycles, phenyl substituted with one or more substituents selected from the group consisting of halogen, haloalkyl, lower alkyl, alkoxy, methylenedioxy, ethylenedioxy, alkylthio, haloalkylthio, thio, hydroxy, cyano, nitro, carboxyl derivatives, phenyloxy, amido, acylamino, amino, alkylamino, dialkylamino, trifluoroalkoxy, trifluoromethylsulfonyl, alkylsulfonyl, sulfonic acid, sulfonamide, phenyl, naphthyl, monocyclic heterocycles, and fused monocyclic heterocycles, monocyclic heterocycles, monocyclic heterocycles substituted with one or more substituents selected from the group consisting of halogen, haloalkyl, lower alkyl, alkoxy, phenyloxy, amino, nitro, hydroxy, carboxyl derivatives, cyano, alkylthio, alkylsulfonyl, phenyl, naphthyl, monocyclic and bicyclic heterocyclicalkyls, and —$SO_2R^{10}$; or X corresponds in structure to Formula (1), and $R^9$ is

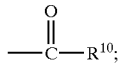

or

X corresponds in structure to Formula (1), and $R^9$ and $R^8$, together with the nitrogen to which they are bonded, form a 4–12 membered mononitrogen-containing monocyclic or bicyclic ring, wherein the ring:
is optionally substituted with one or more substituents selected from the group consisting of lower alkyl, carboxyl derivatives, phenyl, and hydroxy, and
may contain an additional heteroatom selected from the group consisting of O, N, and S; or X corresponds in structure to Formula (3), and $R^9$ is selected from the group consisting of alkylcarbonyl, phenylcarbonyl, alkoxycarbonyl, phenyloxycarbonyl, haloalkylcarbonyl, haloalkoxycarbonyl, alkylthiocarbonyl, phenylthiocarbonyl, or acyloxymethoxycarbonyl; or X corresponds in structure to Formula (4), and both $R^9$ are selected from the group consisting of alkylcarbonyl, phenylcarbonyl, alkoxycarbonyl, phenyloxycarbonyl, haloalkylcarbonyl, haloalkoxycarbonyl, alkylthiocarbonyl, phenylthiocarbonyl, and acyloxymethoxycarbonyl;

as to $Y^1$:
$Y^1$ is selected from the group consisting of alkyl, cycloalkyl, bicycloalkyl, phenyl, monocyclic heterocycles, alkyl substituted with phenyl which can also be substituted with one or more substituents selected from the group consisting of halo, haloalkyl, alkyl, nitro, hydroxy, alkoxy, phenyloxy, phenyl, and naphthyl, phenyl substituted with one or more substituents selected from the group consisting of halo, haloalkyl, hydroxy, alkoxy, phenyloxy, phenyl, naphthyl, nitro, methylenedioxy, ethylenedioxy, and alkyl, alkynyl, alkenyl, —S—$R^{11}$, and —$OR^{11}$; or
$Y^1$ is carbon such that $Y^1$ and $R^8$, together with the atoms to which they are bonded, form a 4–12 membered mononitrogen- or dinitrogen-containing ring optionally substituted with alkyl, phenyl, or hydroxy;

$R^{10}$ is selected from the group consisting of alkyl, phenyl, and monocyclic heterocycles, wherein:
any such substituent is optionally substituted with one or more substituents selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, phenyl, phenyloxy, thio, alkylthio, and monocyclic heterocycles;

as to $R^{11}$:
$R^{11}$ is selected from the group consisting of H, alkyl, phenylalkyl, phenyl, alkenyl, and alkynyl, or
$R^{11}$ and $R^8$, together with the atoms to which they are bonded, form a 4–12 membered mononitrogen- and monosulfur- or monooxygen-containing heterocyclic ring optionally substituted with lower alkyl, hydroxy, phenyl, carboxyl, carboxyl ester, or fused phenyl, or
$R^{11}$ and $R^8$, together with the atoms to which they are bonded, form thiazole, oxazole, benzoxazole, or benzothiazole;

$R^2$, $R^3$, and $R^4$ are independently selected from one or more substituents selected from the group consisting of H, alkyl, hydroxy, alkoxy, phenyloxy, halogen, haloalkyl, haloalkoxy, nitro, amino, alkylamino, acylamino, dialkylamino, cyano, alkylthio, alkylsulfonyl, carboxyl derivatives, trihaloacetamide, acetamide, phenyl, naphthyl, cycloalkyl, thio, monocyclic heterocycles, fused monocyclic heterocycles, and X; and $R^5$, $R^6$, and $R^7$ are independently selected from the group consisting of hydrogen, alkyl, alkenyl, alkynyl, phenyl, carboxyl derivatives, haloalkyl, cycloalkyl, monocyclic heterocycles, monocyclic heterocycles substituted with alkyl, halogen, haloalkyl, cyano, hydroxy, phenyl, naphthyl, nitro, alkoxy, phenyloxy, alkylsulfonyl, phenylsulfonyl, sulfonamide, thio, alkylthio, carboxyl derivatives, amino, amido, alkyl substituted with one or more substituents selected from the group consisting of halo, haloalkyl, hydroxy, alkoxy, phenyloxy, thio, alkylthio, alkynyl, alkenyl, alkyl, phenylthio, alkylsulfoxide, alkylsulfonyl, phenylsulfoxide, phenylsulfonyl, cyano, nitro, amino, alkylamino, dialkylamino, alkylsulfonamide, phenylsulfonamide, acylamide, carboxyl derivatives, sulfonamide, sulfonic acid, phosphonic acid derivatives, phosphinic acid derivatives, phenyl, phenylthio, phenylsulfoxide, and phenylsulfone, all of which are optionally substituted on the phenyl ring with halo, alkyl, haloalkyl, cyano, nitro, hydroxy, carboxyl derivatives, alkoxy, phenyloxy, amino, alkylamino, dialkylamino, amido, phenyl, naphthyl, monocyclic heterocycles, and fused monocyclic heterocycles, monocyclic heterocyclicthio, monocyclic heterocyclicsulfoxide, and monocyclic heterocyclic sulfone, which is optionally substituted with halo, haloalkyl, nitro, hydroxy, alkoxy, naphthyl, or alkyl, alkylcarbonyl, haloalkylcarbonyl, and phenylcarbonyl, phenyl substituted in one or more positions with halo, haloalkyl, alkyl, alkoxy, phenyloxy, methylenedioxy, ethylenedioxy, alkylthio, haloalkylthio, thio, hydroxy, cyano, nitro, acyloxy, carboxyl derivatives, carboxyalkoxy, amido, acylamino, amino, alkylamino, dialkylamino, trifluoroalkoxy, trifluoromethylsulfonyl, alkylsulfonyl, sulfonic acid, sulfonamide, phenyl, naphthyl, monocyclic heterocycles and fused monocyclic heterocycles.

2. A compound, isomer, enantiomer, tautomer, racemate, or polymorph according to claim 1, wherein:

z is 1;
y is 0;
$R^5$ and $R^6$ are each H; and
$R^7$ is H; alkyl, haloalkyl, carboxyalkyl, alkenyl, alkynyl, and phenyl, optionally substituted with one or more halogen atoms.

3. A compound, isomer, enantiomer, tautomer, racemate, or polymorph according to claim 1, wherein:

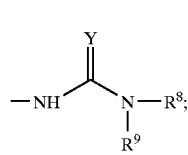

(1)

X is
Y is N—$R^1$;
as to $R^1$ and $R^8$:
  $R^1$ is selected from the group consisting of H, alkyl, phenyl, hydroxy, alkoxy, cyano, and nitro; and $R^8$ is H; or
  $R^1$ and $R^8$, together with the atoms to which they are bonded, form a 4–12 membered dinitrogen-containing heterocycle optionally substituted with one or more substituents selected from the group consisting of lower alkyl, hydroxy, alkoxy, halogen, phenyl, amino, carboxyl, carboxyl ester, and fused phenyl; and
$R^9$ is H.

4. A compound, isomer of the compound, enantiomer of the compound, tautomer of the compound, racemate of the compound, or polymorph of the compound, wherein:

the compound selected from the group consisting of:

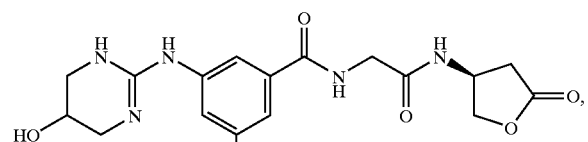

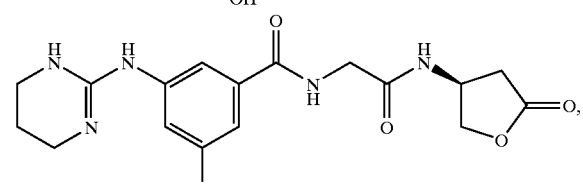

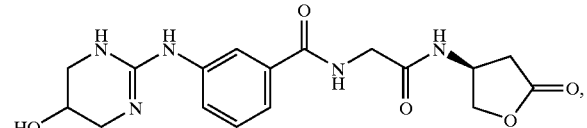

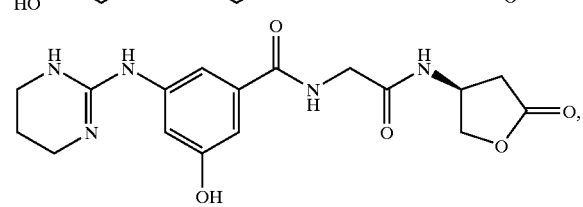

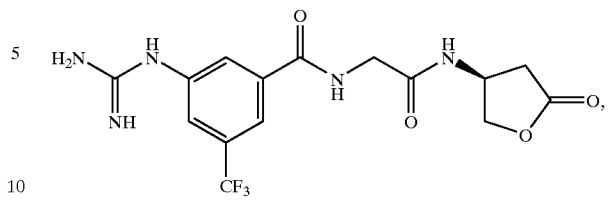

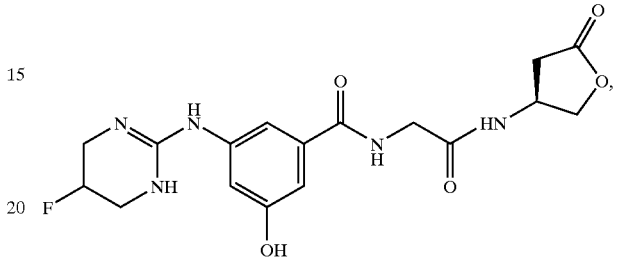

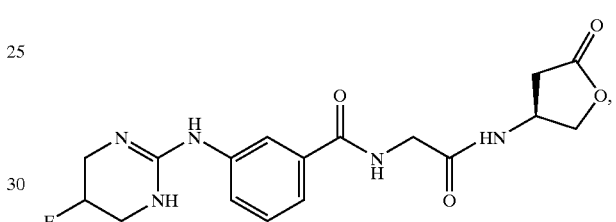

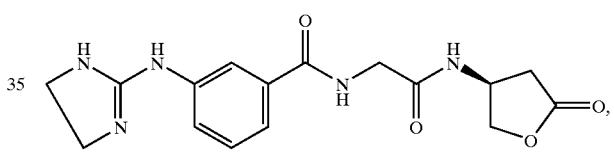

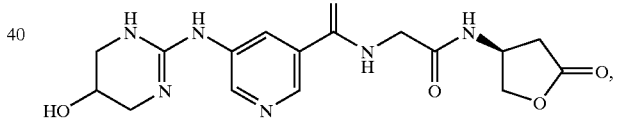

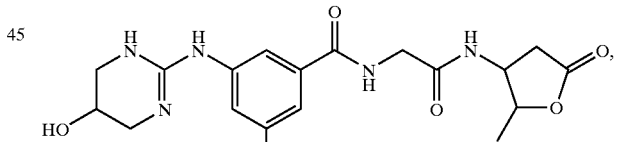

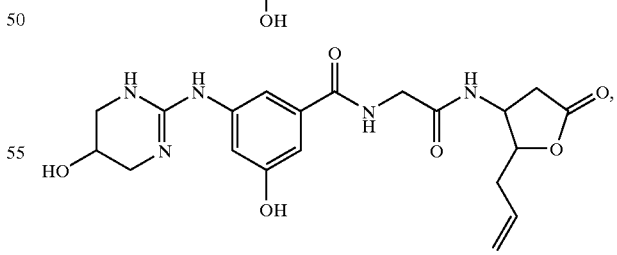

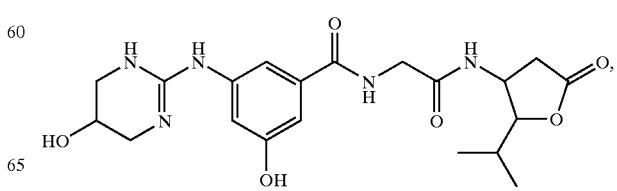

-continued

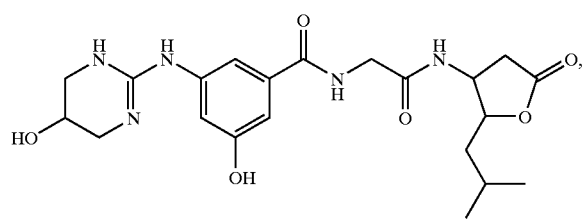
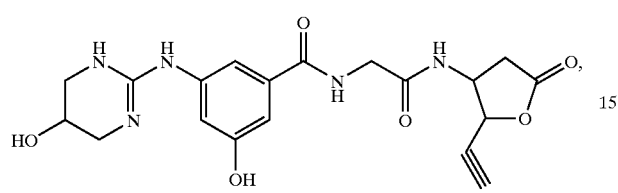
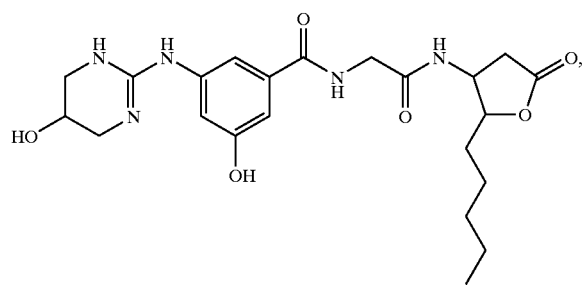
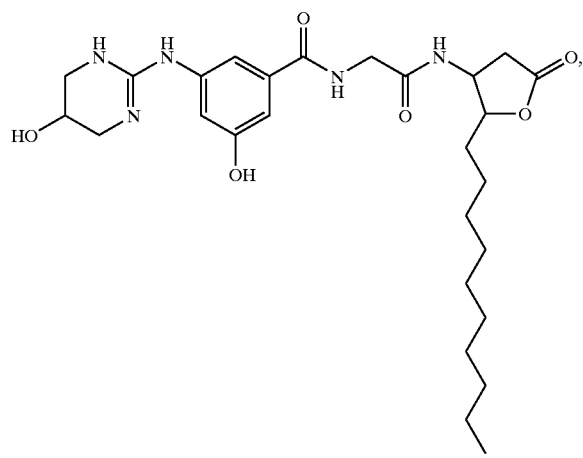
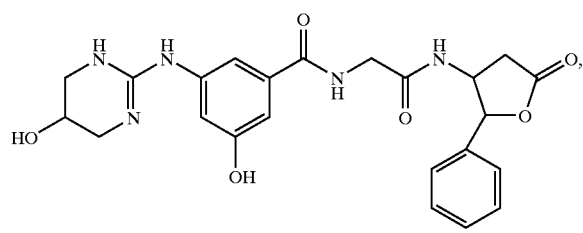
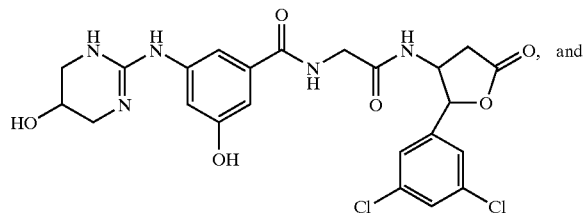

-continued

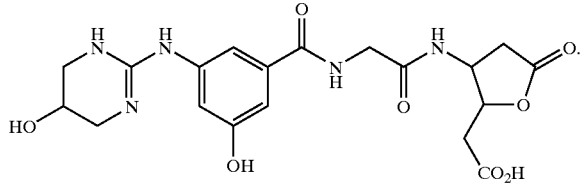

5. A pharmaceutical composition, wherein the composition comprises:
   a compound, isomer, enantiomer, tautomer, racemate, or polymorph of claim 1; and
   a pharmaceutically-acceptable carrier.

6. A method of treating a condition treatable by inhibiting or antagonizing $\alpha_v\beta_3$ or $\alpha_v\beta_5$ integrin, wherein:
   the condition is selected from the group consisting of tumor metastasis, solid tumor growth, angiogenesis, osteoporosis, humoral hypercalcemia of malignancy, smooth muscle cell migration, restenosis, atheroscelososis, macular degeneration, retinopathy, and arthritis; and
   the method comprises administering a therapeutically-effective amount of a compound, isomer, enantiomer, tautomer, racemate, or polymorph of claim 1.

7. A pharmaceutical composition, wherein the composition comprises:
   a compound, isomer, enantiomer, tautomer, racemate, or polymorph of claim 2; and
   a pharmaceutically-acceptable carrier.

8. A method of treating a condition treatable by inhibiting or antagonizing $\alpha_v\beta_3$ or $\alpha_v\beta_5$ integrin, wherein:
   the condition is selected from the group consisting of tumor metastasis, solid tumor growth, angiogenesis, osteoporosis, humoral hypercalcemia of malignancy, smooth muscle cell migration, restenosis, atheroscelososis, macular degeneration, retinopathy, and arthritis; and
   the method comprises administering a therapeutically-effective amount of a compound, isomer, enantiomer, tautomer, racemate, or polymorph of claim 2.

9. A pharmaceutical composition, wherein the composition comprises:
   a compound, isomer, enantiomer, tautomer, racemate, or polymorph of claim 3; and
   a pharmaceutically-acceptable carrier.

10. A method of treating a condition treatable by inhibiting or antagonizing $\alpha_v\beta_3$ or $\alpha_v\beta_5$ integrin, wherein:
   the condition is selected from the group consisting of tumor metastasis, solid tumor growth, angiogenesis, osteoporosis, humoral hypercalcemia of malignancy, smooth muscle cell migration, restenosis, atheroscelososis, macular degeneration, retinopathy, and arthritis; and
   the method comprises administering a therapeutically-effective amount of a compound, isomer, enantiomer, tautomer, racemate, or polymorph of claim 3.

11. A pharmaceutical composition, wherein the composition comprises:
   a compound, isomer, enantiomer, tautomer, racemate, or polymorph of claim 4; and
   a pharmaceutically-acceptable carrier.

12. A method of treating a condition treatable by inhibiting or antagonizing $\alpha_v\beta_3$ or $\alpha_v\beta_5$ integrin, wherein:

the condition is selected from the group consisting of tumor metastasis, solid tumor growth, angiogenesis, osteoporosis, humoral hypercalcemia of malignancy, smooth muscle cell migration, restenosis, atheroscelososis, macular degeneration, retinopathy, and arthritis; and the method comprises administering a therapeutically-effective amount of a compound, isomer, enantiomer, tautomer, racemate, or polymorph of claim 4.

* * * * *